US008460932B2

(12) United States Patent
Lowenstein et al.

(10) Patent No.: US 8,460,932 B2
(45) Date of Patent: Jun. 11, 2013

(54) METHOD OF TREATING A DISORDER BY SUICIDE GENE THERAPY

(75) Inventors: Pedro Lowenstein, Los Angeles, CA (US); Maria Castro, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 544 days.

(21) Appl. No.: 11/444,050

(22) Filed: May 31, 2006

(65) Prior Publication Data

US 2006/0246038 A1 Nov. 2, 2006

Related U.S. Application Data

(60) Division of application No. 10/395,287, filed on Mar. 25, 2003, now abandoned, which is a continuation of application No. 09/693,970, filed on Oct. 23, 2000, now abandoned.

(30) Foreign Application Priority Data

Oct. 21, 1999 (GB) .................................. 9924981.5

(51) Int. Cl.
C12N 15/00 (2006.01)
C12N 15/09 (2006.01)
A61K 48/00 (2006.01)
A61K 35/76 (2006.01)

(52) U.S. Cl.
USPC ............................. 435/455; 424/93.2; 514/44

(58) Field of Classification Search
None
See application file for complete search history.

(56) References Cited

U.S. PATENT DOCUMENTS

| | | | |
|---|---|---|---|
| 5,139,941 A | 8/1992 | Muzyczka et al. | |
| 5,173,414 A | 12/1992 | Lebkowski et al. | |
| 5,501,979 A | 3/1996 | Geller et al. | 435/320.1 |
| 5,554,512 A | 9/1996 | Lyman et al. | |
| 5,750,398 A | 5/1998 | Johnson et al. | 435/375 |
| 5,824,837 A | 10/1998 | Chen et al. | |
| 6,030,956 A | 2/2000 | Boulikas | 514/44 |
| 6,066,624 A | 5/2000 | Woo et al. | 514/44 |
| 6,190,655 B1 | 2/2001 | Lyman et al. | |
| 6,291,661 B1 | 9/2001 | Graddis et al. | |
| 6,365,394 B1 * | 4/2002 | Gao et al. | 435/239 |
| 6,451,593 B1 | 9/2002 | Wittig et al. | |
| 6,518,062 B1 | 2/2003 | Blanche et al. | |
| 6,566,128 B1 | 5/2003 | Graham et al. | |
| 6,630,143 B1 | 10/2003 | Lyman et al. | |
| 6,743,631 B1 | 6/2004 | Mason | |
| 6,818,439 B1 * | 11/2004 | Jolly et al. | 435/320.1 |
| 6,887,688 B2 | 5/2005 | Lagarias et al. | |
| 7,247,297 B2 | 7/2007 | Weichselbaum et al. | |
| 2003/0031681 A1 * | 2/2003 | McCart et al. | 424/186.1 |
| 2004/0009588 A1 | 1/2004 | Chang et al. | |
| 2004/0029227 A1 | 2/2004 | Lowenstein et al. | |
| 2008/0181870 A1 | 7/2008 | Lowenstein et al. | |
| 2010/0143304 A1 | 6/2010 | Lowenstein et al. | |

FOREIGN PATENT DOCUMENTS

| | | |
|---|---|---|
| AU | 9536584 | 5/1996 |
| EP | 1786474 B1 | 6/2011 |
| EP | 2338524 A1 | 6/2011 |
| GB | 2355460 A | 4/2001 |
| GB | 2397063 A | 7/2004 |
| WO | 92/01070 A1 | 1/1992 |
| WO | 93/03769 A1 | 3/1993 |
| WO | 93/04167 A1 | 3/1993 |
| WO | WO-95/09654 | 4/1995 |
| WO | WO 95/09655 | 4/1995 |
| WO | WO 96/12030 | 4/1996 |
| WO | WO-96/20733 | 7/1996 |
| WO | WO-00/65078 | 11/2000 |
| WO | 2006/020949 A2 | 2/2006 |
| WO | 2006/020949 A3 | 2/2006 |
| WO | 96/12030 A1 | 4/2006 |
| WO | 2008/095027 A2 | 8/2008 |

OTHER PUBLICATIONS

Kahle et al, The emerging utility of animal models of chronic neurodegenerative disease, Emerging Therapeutic Targets (2001) 5(1):125-132.*
Check, E, Cancer fears cast doubts on future of gene therapy, Nature,2003, Vo1421, p. 6.*
Thomas et al, Progress and Problems With the Use of Viral Vectors for Gene Therapy, Nature, 346 I May 2003, vol. 4, pp. 346-358.*
Lazic and Barker, Cell-based therapies for disorders of the CNS, Expert Opin. Ther. Patents (2005) 15(10): 1361-137.*
Verma and Somia, Gene Therapy—promises,problems and prospects, Nature, 1997, vol. 389, pp. 239-242.*
Russell, Replicating Vectors for Gene Therapy of Cancer: Risks, Limitations and Prospects, European j Cancer, 1994. vol. 30A(8), pp. 1165-1171.*
Santodonato et al, Local and systemic antitumor response after combined therapy of mouse metastatic tumors with tumor cells expressing IFN-a and HSVtk: perspectives for the generation of cancer vaccines, Gene Therapy (1997) 4, 1246-1255.*
Southgate, T. D., et al., "Long-Term Transgene Expression Within the Anterior Pituitary Gland in Situ: Impact on Circulating Hormone Levels, Cellular and Antibody-Mediated Immune Responses", Endrocrinology (2001), 464-476, vol. 142.
Zermansky, A. J., et al., "Towards Global and Long-Term Neurological Gene Therapy: Unexpected Transgene Dependent, High-Level, and Widespread Distribution of SDV-1, Thymidine Kinase Throughout the CNS", Molecular Therapy (2001), 490-498, vol. 4.
Wang et al, "In Vivo and In Vitro Glioma Cell Killing Induced by an Adenovirus Expressing Both Cytosine Deaminase and Thymidine Kinase and Its Association with Interferon-α", Journal of Neuropathology and Experimental Neurology 58(8):847-858 (1999).

(Continued)

Primary Examiner — Maria Marvich
(74) Attorney, Agent, or Firm — Linda B. Huber; Nixon Peabody LLP

(57) ABSTRACT

The present invention relates to a method of prolonging the expression of an exogenous gene in a cell transduced with the exogenous gene. The method comprises co-administration of the exogenous gene with a herpes virus gene, whereby such co-administration prolongs the expression of the exogenous gene in the transduced cell. The method is particularly useful as a means of effecting gene therapy.

7 Claims, 18 Drawing Sheets

OTHER PUBLICATIONS

O'Malley, Jr. et al, "The Role of Interleukin-2 in Combination Adenovirus Gene Therapy for Head and Neck Cancer", Mol. Endo. 11(6):667-673 (1997).

Felzmann et al, "Characterization of the antitumor immune response generated by treatment of murine tumors with recombinant adenoviruses expressing HSVtk, IL-2, IL-6 or B7-1", Gene Therapy 4:1322-1329 (1997).

Ali et al., Combined Immunostimulation and Conditional Cytotoxic Gene Therapy Provide Long-Term Survival in a Large Glioma Model, Cancer Research, (Aug. 15, 2005), pp. 7194-7204, 65(16).

Ali et al., Inflammatory and Anti-Glioma Effects of an Adenovirus Expressing Human Soluble Fms-Like Tyrosine Kinase 3 Ligand (hsFlt3L): Treatment with hsFlt3L Inhibits Intracranial Glioma Progression, Author Manuscript (published in final version in Molecular Therapy, (Dec. 2004), pp. 1071-1084, 10(6)).

Castro et al., Current and Future Strategies for the Treatment of Malignant Brain Tumors, Pharmacology & Therapeutics, (2003), pp. 71-108, 98.

Chiocca et al., Viral Therapy for Glioblastoma, Cancer Journal, (May-Jun. 2003), pp. 167-179, 9(3).

Cowsill et al., Central Nervous System Toxicity of Two Adenoviral Vectors Encoding Variants of the Herpes Simplex Virus Type 1 Thymidine Kinase: Reduced Cytotoxicity of a Truncated HSV1-TK, Gene Therapy, (2000), pp. 679-685, 7.

Curtin et al., Fms-Like Tyrosine Kinase 3 Ligand Recruits Plasmacytoid Dendritic Cells to the Brain, The Journal of Immunology, (2006), pp. 3566-3577, 176.

Dewey et al., Chronic Brain Inflammation and Persistent Herpes Simplex Virus 1 Thymidine Kinase Expression in Survivors of Syngeneic Glioma Treated by Adenovirus-Mediated Gene Therapy: Implications for Clinica Trials, Nature Medicine, (Nov. 1999), pp. 1256-1263, 5(11).

Dong et al., Antitumor Effect of Secreted Flt3L Can Act At Distant Tumor Sites in a Murine Model of Head and Neck Cancer, Cancer Gene Therapy, (2003), pp. 96-104,10(2).

Fulci et al., Oncolytic Viruses for the Therapy of Brain Tumors and Other Solid Malignancies: A Review, Front Bioscience, (May 1, 2003), pp. 346-360, 8.

Kawashita et al., FLT3-Ligand Gene Transfer Increases Antitumor Effects of Radio-Inducible Suicide Gene Therapy for Hepatocellular Carcinoma, Proceedings of the Annual Meeting for Cancer Research, (2001), 42.

Klatzmann et al., A Phase I/II Study of Herpes Simplex Virus Type I Thymidine Kinase "Suicide" Gene Therapy for Recurrent Glioblastoma. Study Group on Gene Therapy for Glioblastoma, Human Gene Therapy, (Nov. 20, 1998), pp. 2595-2604, 9(17).

Lang et al., Phase I Trial of Adenovirus-Mediated p53 Gene Therapy for Recurrent Glioma: Biological and Clinical Results, Journal of Clinical Oncology, (Jul. 1, 2003), pp. 2508-2518, 21(13).

Lowenstein et al., Immunology of Viral-Vector-Mediated Gene Transfer Into the Brain: An Evolutionary and Developmental Perspective, Trends in Immunology, (Jan. 2002), pp. 23-30, 23(1).

Markert et al., Conditionally Replicating Herpes Simplex Virus Mutant, G207 for the Treatment of Malignant Glioma: Results of a Phase I Trial, Gene Therapy, (2000), pp. 867-874, 7.

Rainov, N.G., A Phase III Clinical Evaluation of Herpes Simplex Virus Type I Thymidine Kinase and Ganciclovir Gene Therapy As an Adjuvant to Surgical Resection and Radiation in Adults With Previously Untreated Glioblastoma Multiforme, Human Gene Therapy, (Nov. 20, 2000), pp. 2389-2401, 11(17).

Rampling et al., Toxicity Evaluation of Replication-Competent Herpes Simplex Virus (ICP 34.5 Null Mutant 1716) in Patients With Recurrent Malignant Glioma, Gene Therapy, (May 2000), pp. 859-866, 7(10).

Sandmair et al., Thymidine Kinase Gene Therapy for Human Malignant Glioma, Using Replication-Deficient Retroviruses or Adenoviruses, Human Gene Therapy, (Nov. 1, 2000), pp. 2197-2205, 11(16).

Thomas et al., Acute Direct Adenoviral Vector Cytotoxicity and Chronic, But Not Acute, Inflammatory Responses Correlate With Decreased Vector-Mediated Transgene Expression in the Brain, Molecular Therapy, (Jan. 2001), pp. 36-46, 3(1).

Zermansky et al., Towards Global and Long-Term Neurological Gene Therapy: Unexpected Transgene Dependent, High-Level, and Widespread Distribution of HSV-1 Thymidine Kinase Throughout the CNS, Molecular Therapy, (Nov. 2001), pp. 490-498, 4(5).

Blackburn et al. Adenoviral Transduction of a Cytosine Deaminase/Thymidine Kinase Fusion Gene into Prostate Carcinoma Cells Enhances Prodrug and Radiation Sensitivity. Int. J. Cancer (1999), 82:239-297.

Borelli et al., Targeting of an Inducible Toxic Phenotype in Animal Celss. Proc. Nat'l Acad. Sci USA (1988), 85:7572-7576.

Dobrovolsky et al. Pms2 deficiency results in increased mutation in the Hprt gene but not the Tk gene of Tk(+/−) transgenic mice. Mutagenesis. (2003), 18(4):365-370.

Fecci P.E et al., Viruses in the Treatment of Brain Tumors. Neuroimaging Clin N. Am (2002), 12(4):553-570.

Galanis et al., Use of Viral Fusogenic Membrane Glycoproteins as Novel Therapeutic Transgene in Gliomas. Human Gene Therapy. (2001), 12(7):811-821.

Gansbacher et al., Interleukin 2 Gene Transfer into Tumor Cells Abrogates Tumorigenicity and Induces Protective Immunity, Journal of Experimental Medicine. (1990), 172:1217-1224.

Golumbek et al., Treatment of Established Renal Cancer by Tumor Cells Engineered to Secrete Interleukin-4. Science. (1981), 254(1):713-716.

King et al., Flt3L mediated gene therapy in a syngeneic model of glioma with and without pre-existing adenoviral immunity. Database Biosis (Online) Biosciences Information Service. (2005), 19(5):A1406.

Lee et al., Gene transfer into human adenocarcinoma cells with an adenoviral vector: Hyperthermia enhances a double suicide gene expression, cytotoxicity and radiotoxicity. Cancer Gene Therapy. (2002), 9:267-274.

O'Malley et al., The Role of Interleukin-2 in Combination Adenovirus Gene Therapy for Head and Neck Cancer. Mol. Endo. (1997). 11(6):667-673.

Minasi et al., The Selective Albation of Interleukin 2-producing Cells Isolated from Transgenic Mice. Journal of Experimental Medicine. (1993), 177:1451-1459.

Tyynela et al., Adenovirus mediated herpes simplex virus thymidine kinase therapy in BT4C glioma mode. Cancer Gene Therapy. (2000), 9:917-924.

Fulci, G. & Chiocca, A.E. The status of gene therapy for brain tumors. Expert Opin Biol Ther. (2007). 7(2):197. doi: 10.1517/14712598.7.2.197. pp. 1-18.

Stone, D. et al. Viral vectors for gene delivery and gene therapy within the endocrine system. Journal of Endocrinology. (2004). 164: pp. 103-118.

* cited by examiner i.p.GCV  i.p. saline

METHOD OF TREATING A DISORDER BY SUICIDE GENE THERAPY

This application claims the benefit of priority under 35 U.S.C. §121 as a divisional of U.S. patent application Ser. No. 10/395,287, filed Mar. 25, 2003, which is a continuation of U.S. patent application Ser. No. 09/693,970, filed Oct. 23, 2000, now abandoned. This application also includes a claim of priority under 35 U.S.C. §119(a) to British patent application No. GB 9924981.5, filed Oct. 21, 1999.

GOVERNMENT RIGHTS

The U.S. Government has a paid-up license in this invention and the right in limited circumstances to require the patent owner to license others on reasonable terms as provided for by the terms of Grant No. R01NS042893 awarded by the National Institutes of Health.

The present invention relates to gene therapy.

Gene therapy is a term used to describe the transfer of one or more genes to a cell. Gene therapy may be used to introduce a gene into a cell and provide for subsequent expression of that gene to alter the phenotype of the cell. For example the gene product may protect the cell from toxic agents, such as chemotherapeutic agents, increase the sensitivity of a cell to a cytotoxic drug, prolong the effect of an agent, either directly or by overcoming some induced or acquired resistance, correct a genetic defect within a target cell or to confer a novel function or property on a target cell.

Successful gene therapy depends upon the efficient delivery of a suitable gene to a target cell and expression of the gene at an adequate level in sufficient target cells to achieve the desired therapeutic endpoint. The duration of expression required will vary between different clinical settings, but in most settings continued therapeutic benefit will depend on targeted, continued, high level, stable and prolonged expression.

Several approaches to gene therapy are under investigation which aim to provide for targeted gene transfer, controlled expression of the gene transferred and enhanced activity of the transferred gene product.

One approach, as described in European Patent Application 90309430.8 in the name of The Wellcome Foundation Limited, is to use chimeric viral vectors systems to provide for targeted gene transfer. In this approach a chimera incorporating a tissue specific transcriptional regulatory sequence (TRS) linked to and controlling the expression of a heterologous enzyme is packaged in a synthetic retroviral particle and used for administration to a patient. The expression of the heterologous gene in the patient is therefore targeted to the target tissue. This approach has been used to target expression of cytotoxic agents, for example thymidine kinase, in cancer cell lines but not in non-cancerous cell lines.

Another approach, as described in International Patent Application PCT/EP98/07380 in the name of Novartis-Erfindungen Verwaltungsaesellschaft MBH, relates to cell-specific expression vectors which allow for controlled expression of the gene transferred. This approach uses an expression vector that contains at least one gene essential for replication of the vector under the control of a heterologous transcriptional regulatory system to produce an expression vector whose replication is controlled by the presence of an agent which controls the activity of the transcriptional regulatory system. This allows the gene expression from the expression vector to be modulated in cells. If, for example vector replication proceeds at levels that are undesirable the approach allows the level of replication to be reduced. This approach has been used to produce an adenovirus vector containing the herpes simplex virus type 1 thymidine kinase gene (ad HSV-1 TK) whose replication is modulated in the presence of ganciclovir (GCV). The vector was administered to subcutaneous tumours induced in a group of mice and after a period of 5 days GCV given to some of the group of mice. Immunohistochemistry of all sacrificed mice showed that HSV1 TK expression was the same between the groups whereas the mice treated with GCV showed diminished vector expression.

A further approach, as described in International Patent Application No. PCT/US98/21672 in the name of Darvin Molecular Corporation relates to expression vectors transferring genes which encode proteins which are mutated with respect to the wild type protein to have increased activity. Such vectors provide a gene product which has enhanced activity within cells transduced with such vectors.

It has been previously proposed that gene therapy may be useful in the treatment of neurological diseases such as Parkinson's disease. Alzheimer's disease and brain tumours. Numerous groups are attempting to develop vector systems that will allow the deliver of potentially therapeutic agents to terminally differentiated neurones within the intact brain. It is also an aim to target gene expression to other brain cell types (e.g. astrocytes and microglia).

The ability of HSV-1 to establish a lifelong latent infection within neurones has led to interest in its use as a neuronal gene delivery vector. However, during HSV-1 latency no viral proteins are produced and transcription from the viral genome is limited to a family of nuclear RNAs, the latency-associated transcripts, whose function is not well understood. Although HSV-1 vectors which express in dorsal root ganglia have been achieved, whether latency can be achieved in cells of the forebrain is yet to be determined.

One viral vector which is particularly used in current gene therapy techniques under study is the adenovirus vector. The ability of the adenovirus vector to transduce most cell types efficiently has resulted in gene therapy trials involving local administration of adenoviral constructs, including administration to brain tissues. The complexity of brain function and the difficulty in non-invasively monitoring and alterations in gene expression in vivo has meant that the extent and duration of the therapeutic benefit of these trials has been difficult to assess.

Clinical trials of conditional cytotoxic gene therapy of glioblastoma are currently ongoing using retro- and adenoviral vectors encoding Herpes simplex virus-1 thymidine kinase (HSV-1-TK), followed by the administration of ganciclovir[1-4]. Much of the efficiency of suicide-gene therapy is thought to be due to the 'bystander effect', of which inflammation and anti-tumour immune stimulation appear to be crucial components[5-7]. In spite of many experimental studies examining the efficiency of suicide-gene therapy-induced glioma regression[8-17], there is no information on the incidence of subsequent chronic brain inflammation. It has been reported previously that brain gene transfer using adenoviral vectors induces acute, short-lived, inflammatory reactions[18-20], although peripheral readministration of viral vectors induces a delayed type hypersensitivity reaction[19], which eliminates transgene expression, and is accompanied by localised demyelination. Likewise, most transgenic protein expression is mostly, though not exclusively, restricted to the injection site. Such experiments have failed to demonstrate widespread expression of transgenic proteins in the brain beyond two months[18,19,21-24]. Understanding the long-term consequences of suicide gene therapy of brain tumours is thus of crucial importance.

It is an aim of the present invention to obviate or mitigate a disadvantage of known gene therapy strategies and to provide a method for prolonged and widespread expression of a gene of interest. A further aim of the present invention is to provide an improved gene therapy treatment.

According to the present invention in a first aspect there is provided a method of prolonging the expression of an exogenous gene in a cell transduced with the exogenous gene, the method comprising co-administration of the exogenous gene with a herpes virus gene, whereby such co-administration prolongs the expression of the exogenous gene in the transduced cell.

According to the present invention in a second aspect there is provided a method of prolonging the expression of an exogenous gene in a cell transduced with the exogenous gene, the method comprising co-administration of the exogenous gene with a conditionally cytotoxic viral gene, whereby such co-administration prolongs the expression of the exogenous gene in the transduced cell.

The invention is based on the inventors' study of the long-term outcomes of adenovirus-mediated conditionally cytotoxic gene therapy in a syngeneic glioblastoma model. CNS-1 cells[25] were implanted into the striatum of Lewis rats, and followed by the injection of adenovirus expressing HSV1-TK, and systemic ganciclovir (GCV). The treatment was very efficient, resulting in the survival of 80-100% of animals for at least 3 months. Unexpectedly, examination of the brains of long-term survivors revealed the presence of chronically active brain inflammation, as well as very strong and widespread HSV1-TK immunoreactivity. These data have important implications for the design and evaluation of clinical gene therapy trials of glioblastoma multiforme.

Based on the results of these experiments the inventors went on to investigate what gave rise to the prolonged and widespread HSV1-TK expression and showed that this was not due to the action of the tumour cells, the adenovirus alone or to the action GCV and therefore proposed that the sustained expression of HSV1 TK may be a previously unknown property of HSV-1 TK which may be applicable to all herpes virus genes or alternatively to all viral conditionally cytotoxic genes.

Accordingly, the inventors propose that the expression of any exogenous gene in a transduced cell may be prolonged if the exogenous gene is co-administered with a herpes virus gene or a viral conditionally cytotoxic gene. This proposal should have enormous impact on the field of gene therapy where it is important to have prolonged expression of a gene of interest. The method according to the present invention thus has utility in a wide range of conditions from cancer to conditions where gene therapy is being considered, such as Parkinson's disease and muscle degeneration for example.

An exogenous gene is defined as a gene or gene fragment which is provided to a transduced cell. The exogenous gene may be one that is not normally expressed in the cell which is transduced. Alternatively, the exogenous gene may be one that is expressed by the cell that is transduced.

It is well known that genes may be introduced into cells in various ways.

The exogenous gene and/or herpes virus gene may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to an area topically or by injection.

According to one embodiment of the first aspect of the present invention the exogenous gene and herpes virus gene or conditionally cytotoxic gene may be introduced into the cell as "naked" genes by standard physical means including direct endocytotic uptake.

The "naked" exogenous gene, herpes virus gene/conditionally cytotoxic gene or both may be delivered to the cell as separate pieces of nucleic acid. If the exogenous gene and herpes virus gene/conditionally cytotoxic gene are delivered to the cell together they may be provided on one piece of DNA as a chimera encoding the two full length gene products. The "naked" DNA for the exogenous gene and/or herpes virus gene/conditionally cytotoxic gene may be further incorporated within a liposome or virus particle for delivery to a cell.

According to an alternative embodiment of the first and second aspects of the present invention, the exogenous gene, herpes virus gene/conditionally cytotoxic gene or both may be introduced into the cell via a recombinant vector delivery system. The vector may for example be a plasmid, cosmid or phage. Such recombinant vectors are highly useful according to the first and second aspects of the present invention for transducing cells with the exogenous gene and the herpes gene/conditionally cytotoxic gene.

The exogenous gene and herpes virus gene/conditionally cytotoxic gene may be co-administered to a cell in one vector or in two separate vectors. If provided in one vector the two genes may be arranged to provide a linked transcript under the control of the same regulatory elements if present or may be provided in separate regions of the vector. If provided in two separate vectors it is preferred that the vectors should be arranged to transduce the same cell population.

A vector refers to an assembly which is capable of directing the expression of a gene. Recombinant vectors may also include functional elements. For instance, recombinant vectors can be designed such that the vector will autonomously replicate in the nucleus of the cell. In this case, elements which induce DNA replication may be required in the recombinant vector. Alternatively the recombinant vector may be designed such that the vector and exogenous gene and/or herpes virus gene/conditionally cytotoxic gene integrate into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required. The recombinant vector may further be a virion or a transcriptionally targeted vector which specifically restricts expression to a particular tissue or cell type.

The exogenous gene and or herpes virus gene may (but not necessarily) be one which becomes incorporated in the DNA of cells of the subject being treated. Undifferentiated cells may be stably transduced leading to the production of genetically modified daughter cells (in which case regulation of expression in the subject may be required e.g. with specific transcription factors or gene activators).

Preferred vector systems for use according to the first aspect of the present invention are viral vector systems in which the vector is derived from a DNA virus, for example, parvovirus, picornavirus, pseudorabies virus, hepatitis virus A, B or C, papillomavirus, papovavirus (such as polyoma and SV40) or herpes virus (such as Epstein-Barr Virus, Varicella Zoster Virus, Cytomegalovirus, Herpes Zoster and Herpes Simplex Virus types 1 and 2), an RNA virus or a retrovirus, such as the Moloney murine leukemia virus or a lentivirus (i.e. derived from Human Immunodeficiency Virus, Feline Immunodeficiency Virus, equine infectious anaemia virus. etc.).

A particularly preferred vector system for use according to the first aspect of the present invention is the adenovirus vector system. A preferred adenovirus vector system is described in International Application No. PCT/EP98/07380.

The viral vector particles comprising either the exogenous gene, the herpes virus gene/conditionally cytotoxic gene or both may be administered to a host. The host may be an animal host, including mammalian, non-human primate, rodent and human hosts.

The viral particles may be administered in combination with a pharmaceutically acceptable carrier suitable for administration to a patient. The carrier may be a liquid carrier (for example saline solution) or a solid carrier, such as for example microcarrier beads.

The herpes virus gene which is co-administered to prolong expression of an exogenous gene in a cell is preferable any gene encoded by the genome of the family Herpesviridae. Representative examples of this family include Herpes Simplex Virus Type 1, Herpes Simplex Virus Type 2, Varicella Zoster Virus, human and murine cytomegalovirus, Pseudorabies virus, Marek's disease virus, cercopitecine herpes virus and Epstein Barr virus.

If the herpes virus gene is to be administered on a herpes viral vector it is preferred that the herpes virus gene is heterologous to the herpes virus vector. The term "heterologous" means that the herpes virus gene is not found naturally in the native herpes vector.

A preferred herpes gene that is administered to prolong gene expression of a co-administered exogenous gene is a herpes virus thymidine kinase gene or variant thereof. The herpes virus TK gene encodes a viral TK protein which is important in the synthesis of nucleic acid precursors normally within cells infected with herpes virus.

In herpes virus infected cells TK can phosphorylate the guanosine analogue ganciclovir (GCV) resulting in GCV-monophosphate, in contrast to uninfected cells which contain a cellular TK gene which does not act on GCV. GCV monophosphate, if produced is phosphorylated by intracellular protein kinases producing a GCV-triphosphate in cells which contain the herpes virus TK gene. The GCV-triphosphate is preferably incorporated into the DNA of rapidly dividing cells (e.g. cancer cells) but due to its chemical structure cannot promote further elongation of nascent DNA resulting in chain termination and cell death.

Various mutant forms of herpes virus TK have been proposed all of which have varying degrees of TK activity. The use of such mutants, as described in International Patent Application No. PCT/US98/21672 is envisaged within the scope of the first aspect of the present invention.

Other herpes virus genes that are preferred to prolong gene expression of a co-administered exogenous gene is herpes virus ribonucleotide reductase, an enzyme involved in purine metabolism.

It may be that the addition of a pro-drug to the cell transduced according to the method of the first or second aspects of the invention may enhance the prolonged expression of the exogenous gene. Therefore, preferably, the method according to the first and second aspects of the invention further comprises addition of a pro-drug to the transduced cell.

Examples of suitable pro-drugs include nucleoside analogues which may be pro-drugs activated by herpes virus TK or other, non herpes virus conditionally cytotoxic enzymes include purine arabinosides and substituted pyrimidine compounds, for example as described in published European Patent Application EP-A415 731. Representative examples of nucleoside analogues include GCV, aciclovir, trifluorothymidine, 1-[2-deoxy, 2-fluoro, β-D-arabino furanosyl]-5-iodouracil, ara-A, ara-T. 1-β-D-arabinofuranoxyl thymine, 5-ethyl-2'deoxyuridine, 5-iodo-5'-amino-2,5'-dideoxyuridine, idoxuridine, AZT, AIU (5-iodo-5' amino 2',5'-dideoxyuridine), dideoxycytidine and Ara-C.

As described above herpes virus TK is a conditionally cytotoxic enzyme which can act on a non-toxic compound, GCV (a nucleoside analogue pro-drug) to produce a compound which is toxic to a cell, GCV triphosphate (a nucleoside analogue drug).

Other non-herpes virus genes which encode an enzyme which is conditionally cytotoxic and act on a pro-drug to produce a drug will be known to persons skilled in the art, and are included within the scope of the second aspect of the invention. Such conditionally cytotoxic enzymes include thymidine kinase from sources other than herpes virus, carboxypeptidase G2, alkaline phosphatase, penicillin—V amidase and cytosine deaminase gene.

Other nucleoside analogues which may be pro-drugs activated by herpes virus TK or other, non herpes virus conditionally cytotoxic enzymes include purine arabinosides and substituted pyrimidine compounds, for example as described in published European Patent Application EP-A415 731. Representative examples of nucleoside analogues include GCV, acyclovir, trifluorothymidine, 1-[2-deoxy. 2-fluoro. β-D-arabino furanosyl]-5-iodouracil, ara-A, ara-T, 1-β-D-arabinofuranoxyl thymine, 5-ethyl-2'deoxyuridine, 5-iodo-5'-amino-2,5'-dideoxyuridine, idoxuridine, AZT, AIU (5-iodo-5' amino 2',5'-dideoxyuridine), dideoxycytidine and Ara-C.

The nature of the exogenous gene to be co-administered with the herpes virus gene/conditionally cytotoxic gene for prolonged expression will depend upon why prolonged expression is desired. If for example the method is for gene therapy of a particular disease the exogenous gene will be a therapeutic gene whose expression is known to be associated with treatment of that disease.

If the method is used to study the distribution or expression of a particular gene in a cell, tissue or organ, the exogenous gene co-administered with the herpes virus gene/conditionally cytotoxic gene for prolonged expression is a marker gene.

Preferred genes to be administered according to the first aspect and second aspects of the present invention include those encoding glial cell derived growth factor (GDNF), neurotrophic factor (NGF), neurturin, persefin and other members of the Transforming growth factor β superfamily, Nurr-1, gli-1, gli-3, brain derived neurotrophic factor, ciliary derived neurotrophic factor (CNTF), amyloid precursor protein, marker genes like β galactosidase, green fluorescent protein (s) (GFP) amongst others, transducing growth factors β1, β2, β3, inhibitors of NF kappaB, anti-apoptotic genes. e.g. bcl-2, bcl-x1, anti-inflammatory and immune-modulators such as interleukin 1 receptor agonist (IL-Ira), IL-receptor 2, neuropeptide neurotransmitters, e.g. corticotrophin releasing hormone, substance P, neurokinins, etc.

As the method according to the first and second aspects of the present invention may provide for widespread distribution of the herpes gene/conditionally cytotoxic gene and exogenous gene in brain tissues, the method according to the first and second aspects of the present invention are proposed to be particularly useful in gene therapy for brain diseases. In such therapy it is preferred that the exogenous gene encodes a therapeutic agent associated with such brain diseases. Such genes may include those provided above.

Accordingly a third aspect of the invention provides for the use of a herpes virus gene co-administered with a heterologous gene for prophylaxis or treatment of a disease associated with body tissues.

Accordingly a fourth aspect of the invention provides for the use of a conditionally cytotoxic gene co-administered with a heterologous gene for prophylaxis or treatment of a disease associated with body tissues.

Particular brain diseases which the third and fourth aspects of the invention seek to treat include brain tumours, Alzheimer's disease, Parkinson's disease, Huntington's disease, lateral amyotrophic sclerosis, neurodegenerative and neurometabolic disorders, chronic brain infections (e.g. HIV, measles, etc.), pituitary tumours, spinal cord degeneration (both inherited and traumatic), spinal cord regeneration, autoimmune diseases (e.g. multiple sclerosis, Guillain Barre syndrome, peripheral neuropathies, etc.) and any other diseases of the brain known to persons skilled in the art.

Treatment of diseases associated with tissues of the body other than the brain are also envisaged within the scope of the third and fourth aspects of the present invention, such as the liver, muscle, etc.

The inventors propose that as well as prolonging gene expression, the co-administered herpes gene/conditionally cytotoxic gene provides more widespread distribution of a gene administered by gene therapy than in the absence of the herpes virus gene. Histological studies show that a HSV1 TK gene is expressed in the axons, dendrites and cell bodies of neurones in the contralateral side to the side of the brain in which a viral vector was injected. This is in sharp contrast to the observed effects of steroids on adenoviral vectors where the encoded transgene expression was found to be local and the majority of the herpes gene was found in astrocytes and not in neurones. In the treatment of neuronal diseases such as Parkinson's disease for example, it is essential that the expression of the exogenous gene, for example in this case a dopamine receptor or dopamine agonist is in the neurones and not astroslial cells. Accordingly the third aspect of the invention has particular utility in the treatment of brain diseases.

The findings of the inventors have implications in currently advised treatment regimes involving gene therapy methods. For example, a trial is underway regarding administering an adenoviral vector containing a herpes virus TK gene together with GCV (so-called suicide gene therapy) in a single treatment cycle for GCV of up to two weeks. The methods underlying this trial are described in International Patent Application PCT/US98/21672.

According to current thinking it would be assumed that the TK administered to a patient in a gene therapy method (e.g. by an adenovirus vector) would be only transiently expressed and therefore it would only be worthwhile providing a GCV treatment cycle for a short period after administration of the TK. According to the inventors' findings the TK expression would be stable and could last for up to 12 months from introduction of the TK gene by gene therapy. Thus, based on these findings the number of cycles of clinical treatment with GCV should be increased as compared to currently proposed treatment regimes.

According to the present invention in a fifth aspect there is provided a method for the treatment of a disorder by suicide gene therapy comprising more than one cycle of administration of a cytotoxic pro-drug.

As it has been shown that the herpes virus TK gene is still expressed after one year it is apparent that current treatment regimes with TK and GCV of one two week cycle of administration of GCV are curtailed prematurely. Additional cycles of administration of GCV at one month, two months, three months, up to or more than 12 months, from the administration of the TK gene could still give therapeutic effect as the TK gene will still be expressed in vivo.

BRIEF DESCRIPTION OF THE DRAWINGS

The invention will now be described by way of example only, with reference to the following drawings, in which.

EXAMPLES

Methods

Figure 1:
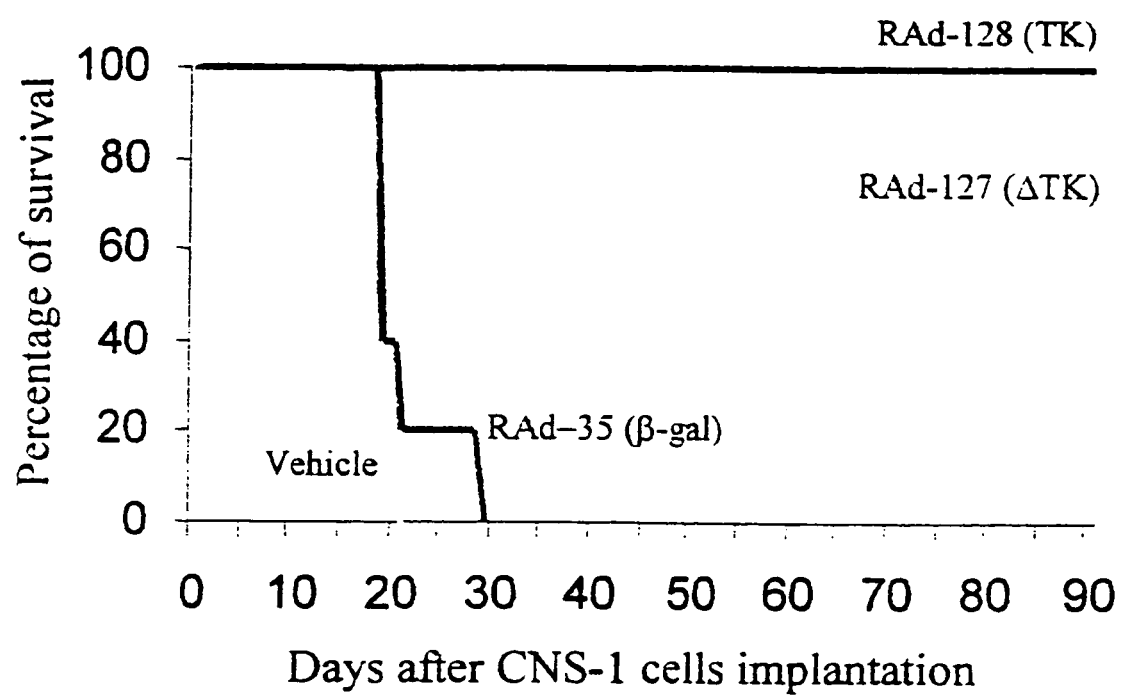
FIG. 1 shows survival analysis of Lewis rats implanted with CNS-1 cells, and treated with RAd-128 (TK), RAd-127 (ΔTK), Rad-35 (βgal), or vehicle, and GCV.

Cell Culture. The rat glioma cell line CNS-1 was kindly provided by Prof. W. Hickey (Dartmouth Medical Center, Department of Pathology, Lebanon, N.H., USA)[25]. The kidney embryonic cell line 293 was obtained from Microbix Biosystems Inc. (Toronto, Ontario, Canada). The maintenance of the cell lines was described previously[37,38].

Adenovirus vectors expressing HSV1-TK, HSV1-ΔTK, or β-galactosidase RAd vectors encoding HSV1-TK (RAd-128) and HSV1-ΔTK (RAd-127) under the short immediate/early human cytomegalovirus (sMIEhCMV) promoter[37,38] were generated and characterised as described previously[27-28]. Viruses were purified using double caesium chloride gradient and titres of $1\times10^{10}$–$1\times10^{11}$ infectious units (IU)/ml, and particle/pfu ratios of 30 were obtained as described in detail elsewhere[17,20,27,28,37,38]. As control virus, a double caesium chloride gradient purified adenovirus, RAd-35, expressing the E. coli β-galactosidase gene driven by the sMIEhCMV promoter, was used[38]. We have reported elsewhere that in vitro, CNS-1 cells did express the transgene HSV1-TK following infection with adenoviral vectors, and were sensitive to apoptosis induced following the addition of ganciclovir to infected cultures[27,28].

Lipopolysaccharide endotoxin (LPS) assay and replication competent adenovirus (RCA) assays LPS contamination in each RAd stock was assessed by using the amoebocyte horseshoe crab lysate method (E-Toxate assay, Sigma, Poole, Dorset, UK)[39]. RAd-127 and RAd-128 showed levels of LPS below 5 milli-endotoxin units (mEU)/μl; thus, in the 4 μl injected total LPS was below 20 mEU. β-galactosidase expressing RAd-35, showed levels of LPS≦r2 mEU/μl; thus, in the 4 μl injected total LPS was ≦8 mEU. The amount of LPS needed to produce inflammatory responses in the brain is several fold above the upper limit of bioactive LPS activity value obtained in our bio-assays[40]. Our viral volumes injected were essentially LPS free. RCA presence was tested by the supernatant rescue assay[41]. No RCA was detected in $2.6\times10^8$ IU of either of the RAd-127 and RAd-128 vector stocks used in our experiments, showing the absence of RCA in an amount of vector three times higher than the total amount of infectious units that were injected in vivo.

In vivo treatment of gliomas. Male Lewis rats (250-300 g) were anesthetized with halothane (Zeneca Ltd., Macclesfield, Cheshire, UK) and placed in a stereotaxic frame. A burr hole in the skull was made with a drill 3 mm to the right and 1 mm anterior to bregma. A 5 μl syringe fitted with a 26 gauge needle was connected to the manipulating arm of a stereotaxic frame, and 5 or $10\times10^3$ CNS-1 cells (in 3 μl of phosphate buffered saline (PBS) were injected over a 3 min period into the striatum at the following location: bregma +1 mm; lateral +3 mm: ventral −4 mm. The needle was left in place for another 5 min before removing.

Viruses were injected into the tumour site three days after tumour implantation. Using the same anterior and lateral coordinates, 1 µl of PBS or 1 µl (2×10$^7$ IU/µl) of RAd-127, RAd-128 or RAd-35 were injected at each of the following ventral coordinates: −5 mm; −4.5 mm: −4 mm; −3.5 mm. Starting 12 hours after the injection of the viral vector, 25 mg/kg of ganciclovir (GCV) (Cymevene, Roche Products Ltd., Welwyn Garden City, UK) was injected intra-peritoneally twice daily for 7 days. Animals injected with RAd-127, RAd-128, RAd-35 or PBS (n=5 per group) were monitored daily. Any animal showing any sign of morbidity, was perfusion-fixed and brains were removed for histological analysis.

In other groups of animals not implanted with CNS-1 tumours, the same amount of RAd-128 was injected into the brain, and was followed by ganciclovir or saline administration for 7 days (n=3 per group). Animals were perfused either at 1 or 3 months post-adenoviral vector injection.

Histological Analysis, Fixation, Paraffin and Plastic Sections

Rats were anaesthetised, and fixed by cardiac perfusion. First, animals were perfused with approximately 100 ml of Tyrode solution (0.14 M NaCl, 2.7 mM KCl, 1.8 mM CaCl$_2$, 0.32 mM NaH$_2$PO$_4$, 5.6 mM glucose and 11.6 mM NaHCO$_3$), containing heparin (10 units/ml) (CP Pharmaceuticals Ltd., Wrexham, UK), and this was followed by 250 ml of 4% paraformaldehyde in PBS, pH 7.4. Brains were removed and placed in 4% paraformaldehyde for 24 h. Serial Vibratome sections (70 µm) were maintained at 4° C. in PBS. Sections were stained with hematoxylin and eosin, or Luxol fast blue, or processed by immunohistochemistry. Alternatively, some animals were perfused with 1% glutaraldehyde, 2% paraformaldehyde in 0.1M phosphate buffer, pH 7.4, and post-fixed for 2-3 days. Some of the paraformaldehyde fixed brains were dissected, and tissue blocks containing the needle track were embedded on paraffin. Serial sections were performed on each block to define precisely the location of the injection area. Five micron thick paraffin sections were stained with hematoxylin and eosin. Luxol fast blue myelin stain, and Bielschowski silver impregnation for axons. Immunocytochemistry was performed using the avidin-biotin technique, using the following primary antibodies: W3/13 (leucosyalin, mouse monoclonal staining of rat T cells, Serotec): OX8 (mouse monoclonal antibodies recognising CD8+ T-lymphocytes, Serotec); and cyclic nucleotide phosphodiesterase (CNPase; mouse monoclonal SMI 91). Glutaraldehyde fixed tissue was dissected into small tissue blocks containing the injection site. Material was then further fixed/stained in 1% osmic acid in phosphate buffered saline, and embedded into Epon; 0.5 µm thick plastic sections were stained with toluidine blue.

Immunohistochemistry on Vibratome Sections

Immunohistochemistry was performed on free floating sections, as described before[36,42]. Anti-GFAP (Boehringer Mannheim Ltd., Lewes, East Sussex, UK) and anti-vimentin antibodies (Sigma, Poole, Dorset, UK), specific for astrocyte-specific intermediate filaments, were used to identify astrocytes, and β-tubulin III (Sigma, Poole, Dorset, UK), to detect neurons and their axons. Anti-ED1 antibodies, to identify monocytes/macrophages/microglial cells, anti-CD3 antibodies to detect total lymphocytes, and anti-CD8 antibodies, which detect CD8 positive lymphocytes and NK cells, were from Serotec Ltd., Kidlington, Oxford. UK. HSV1-TK proteins were detected using an anti-HSV1-TK polyclonal antibody (kindly provided by M. Janicot. Rhone Poulenc Rorer, Paris, France). Sections were washed twice with Tris buffered saline (TBS) (50 mM Tris; 0.9% NaCl; 0.5% Triton; pH 7.4), incubated for 15 min with 0.3% H2O2, washed three times with 2 ml of TBS, incubated with 10% horse normal serum (HNS, Life Technologies Ltd., Inchinnan Business Park, Paisley, UK) in TBS for 45 min, and washed briefly for 10 min with 1% NHS in TBS. Sections were then incubated overnight at room temperature with primary antibodies at the following concentration: anti-GFAP dilution 1/200, monoclonal anti-vimentin clone V9 (1/1000), anti-ED-1 (1/1000), anti-CD3 (1/500), anti-CD8 (1/500), anti-_-tubulin III (1/2000), and polyclonal anti-HSV1-TK (1/1000). Antibodies were diluted in 1% NHS in TBS. The following day, sections were washed three times with TBS before incubation with a 1/200 dilution of the secondary antibody (rabbit anti-mouse immunoglobulins biotinylated. Dako Ltd., High Wycombe, Bucks, UK) for 4 h at room temperature. Sections were then washed three times with TBS before incubation with Avidin/Biotin complex (Vectastain ABC Kit, Vector Laboratories, Bretton, Peterborough, UK) for 3 h at room temperature. Subsequently, sections were washed three times with PBS and two additional times with 0.1 M acetate buffer, pH 6.

Staining was developed by incubating the sections for 5 min at room temperature with a solution containing equal volumes of: (i) 0.2 M acetate buffer pH 6 containing 48 g/l ammonium nickel sulphate, 4 g/l glucose, 0.8 g/l ammonium chloride, and, (ii) 1 g/l 3,3'-diaminobenzidine and 50 mg/l glucose oxidase in distilled water. The staining reaction was stopped by washing the sections two times in 0.1 M acetate buffer pH 6 and two additional times in PBS. Sections were placed on gelatin coated slides, dehydrated, coverslipped and mounted.

Statistical Analysis

Survival data were analysed by Kaplan-Meier estimator analysis, and compared using the generalised Wilcoxon test (Prentice-Peto).

Magnetic Resonance Imagining

Proton magnetic resonance imaging of the rat brain was performed with a 4.7 T, 15 cm horizontal bore Biospec (Bruker/Oxford Instruments) system, using a 2.5 cm surface coil. During imaging, animals were maintained under general anaesthesia by means of a Halothane (Zeneca Ltd., Macclesfield, Cheshire, UK)/oxygen gas mixture. In order to detect the presence of tumours in the brain, axial images, of 2 mm slice thickness, were acquired at approximately 2 mm intervals. The position of the slice of interest, relative to the plane of coil, was selected by applying a 90° "hard" pulse of between 35 and 90 µs duration. In preliminary studies, $T_1$, $T_2$, magnetisation transfer contrast (MTC) and diffusion-weighted pulse sequences were compared, in order to determine the conditions required to give optimum contrast between tumour and normal brain tissue. While the tumours were detectable in $T_2$-weighted images, MTC[43,44] provided greater contrast and was used in all subsequent experiments. The MTC sequence involved the application of a pulse of radiation on 1 s duration, with an offset of 5 kHz and an amplitude of 1.5×10$^{-5}$ T. In-plane resolution was 240×480 µm for a field of view of 6.2 cm. The superiority of this imaging technique in the detection of gliomas has been demonstrated previously[45].

Detection of Adenoviral Genome in Brain Sections Using PCR

Adenoviral sequences were detected in free-floating vibratome-cut brain sections using the polymerase chain reaction (PCR). Briefly, sections were digested for 24 hours at 37° C. in 10 mM Tris-HCl (pH8), 10 mM NaCl, 25 mM EDTA, 1% SDS and 4 mg/ml proteinase K. The proteinase K was heat inactivated at 95° C. for 10 minutes after which two rounds of phenol:chloroform:isoamyl alcohol (25:24:1) extraction were carried out. The genomic DNA was then ethanol precipitated with 3M sodium acetate (pH 5.2), washed with 70% ethanol and then re-suspended in sterile water containing 20 μg/ml DNase-free RNase.

Ad 5 transcription unit IVa2, Ad 5 E1B, HSV-1 TK and β-actin sequences were detected using four different primer sets. Primers A and B (FIG. 5c) are specific to the IVa2 transcription unit of the Ad 5 genome and produce a PCR product of 686 bp. Primers C and D (FIG. 5c) are specific to the E1B transcription unit of the Ad 5 genome and produce a PCR product of 560 bp[35]. Primers E and F (FIG. 5c) are specific to HSV-1 TK and produce a PCR product of 365 bp from TK and ΔTK. Primers G and H have been modified from a method for detecting chicken β-actin[46] and produce a PCR product of 340 bp from exon 4 of rat cytoplasmic β-actin. In a 50 μl PCR reaction, 5-10 μl of genomic DNA was used in a solution containing 1×PCR buffer (Promega, Southampton, UK), 200 μM dTTP, 200 μl dTTP, 200 μM dCTP, 200 μM dGTP, 2 mM $MgCl_2$, 2 ng/ml each primer and 1U Taq polymerase (Promega, Southampton, UK). PCR conditions were 35 cycles of: 30 seconds denature, 30 seconds anneal, and 1 minute extension followed by a further 10 minutes extension. The annealing temperatures for primer pairs a/b, c/d, e/f and g/h were 56° C., 57° C., 63° C. and 63° C. respectively. The PCR products were separated on a 2% agarose gel and visualised on a UV transilluminator using ethidium bromide staining.

Sequences were as follows;

```
A: 5'-AAGCAAGTGTCTTGCTGTCT-3';     (SEQ ID NO. 1)

B: 5'-GGATGGAACCATTATACCGC-3';     (SEQ ID NO. 2)

C: 5'-CAAGAATCGCCTGCTACTGTTGTC-3'; (SEQ ID NO. 3)

D: 5'-CCTATCCTCCGTATCTATCTCCACC-3';(SEQ ID NO. 4)

E: 5'-AAAACCACCACCACGCAACT-3';     (SEQ ID NO. 5)

F: 5'-GTCATGCTGCCCATAAGGTA-3';     (SEQ ID NO. 6)

G: 5'-CCAGCCATGTACGTAGCCATCC-3';   (SEQ ID NO. 7)

H: 5'-GCAGCTCATAGCTCTTCTCCAGG-3'.  (SEQ ID NO. 8)
```

Peripheral Priming with CNS-1 Cells

CNS-1 cells were treated with 2 μg/ml mitomycin C overnight to arrest cell division. Twenty-five thousand mitomycin C treated CNS-1 cells (primed rats), or PBS (controls), was injected subcutaneously into the flank of Lewis rats (n=4, per each group). Thirty days later all animals were rechallenged by implanting 5,000 CNS-1 cells into the striatum, unilaterally. All animals primed peripherally with mitomycin C treated CNS-1 cells survived, while those primed with PBS died by day 30 post-tumour implantation. Surviving animals were perfused 90 days after intracerebral challenge.

Results

Adenovirus Encoding HSV-1 TK Plus Ganciclovir, Inhibits the Growth of CNS-1 Gliomas Implanted into the Brains of Syngeneic Lewis Rats Implantation of 5000 CNS-1 cells unilaterally into the striatum of Lewis rats killed animals within 30 days (FIG. 1). Injection of $8\times10^7$ infectious units (IU) of a replication-defective recombinant adenovirus (RAd) expressing either the full length HSV1-TK gene (RAd-128), or a truncated, biologically active HSV1-TK gene of reduced intrinsic toxicity[26-28]-HSV1-(TK(RAd-127), into the same site at 3 days post-implantation, followed by ganciclovir treatment for seven days, almost completely inhibited CNS-1 glioma growth. Animals were monitored by weekly magnetic resonance imaging (MRI) brain scans to assess treatment effectiveness. Tumour growth was only seen in a single animal treated with RAd-127. No MRI, clinical, or anatomical evidence of tumour growth was observed in any other animals. Survival at 3 months post tumour implantation was 100% in animals injected with RAd-128 and 83-100% in animals injected with RAd-127 (survival of animals injected with RAd-127 shown in FIG. 1 was 83%). The survival rates of animals injected with either RAd-128 or RAd-127 were significantly better than of those animals treated with either RAd-35, an adenovirus vector expressing (-galactosidase, or vehicle alone (p=0.0079). No significant differences were observed in the survival either between vehicle and RAd-35 treated groups (p=0.1232), or between groups of animals treated with either RAd-128 or RAd-127 (p=0.3613). In two identical repeat experiments, no tumour growth was detected in animals treated with either RAd128 or RAd127.

Chronic Active Inflammation following the Complete Inhibition of CNS-1 Tumour Growth by Gene Therapy: Astrocytosis, Microglia/Macrophage and Lymphocyte Infiltration, and Loss of Myelinated Fibres.

General histopatlological analysis Long-term (ninety days) survivors in our experimental syngeneic glioma trials were perfusion-fixed, and their brains analysed histopathologically for the distribution of glial, inflammatory, and immune cell markers, as well as for the integrity of myelin fibres and oligodendrocytes.

Examination of haematoxylin and eosin stained sections revealed the presence of inflammatory infiltrates (i.e. diffuse hypercellularity within the white matter, striatum and perivascular cuffs), and lateral ventricle enlargement (also detected by MRI), ipsilateral to tumour and viral vector injection (FIG. 2a, b).

Astrocytosis Immunohistochemical staining for the astrocyte markers vimentin (FIG. 2c, d) and glial fibrillary acidic protein (GFAP) (FIG. 2e, f) indicated a widespread activation of astrocytes. GFAP is expressed by astrocytes, and is upregulated upon activation. Vimentin is undetectable in resting adult rodent astrocytes, but is also upregulated upon activation. Astrocyte activation was bilateral, but was strongest in the ipsilateral subcortical white matter. Vimentin-positive cells displayed typical astrocytic morphology, with perivascular end-feet. The distribution of activated GFAP immunoreactive astrocytes was much wider than the area occupied by vimentin-immunopositive cells. Astrocyte activation was seen in all animals.

Figure 2:
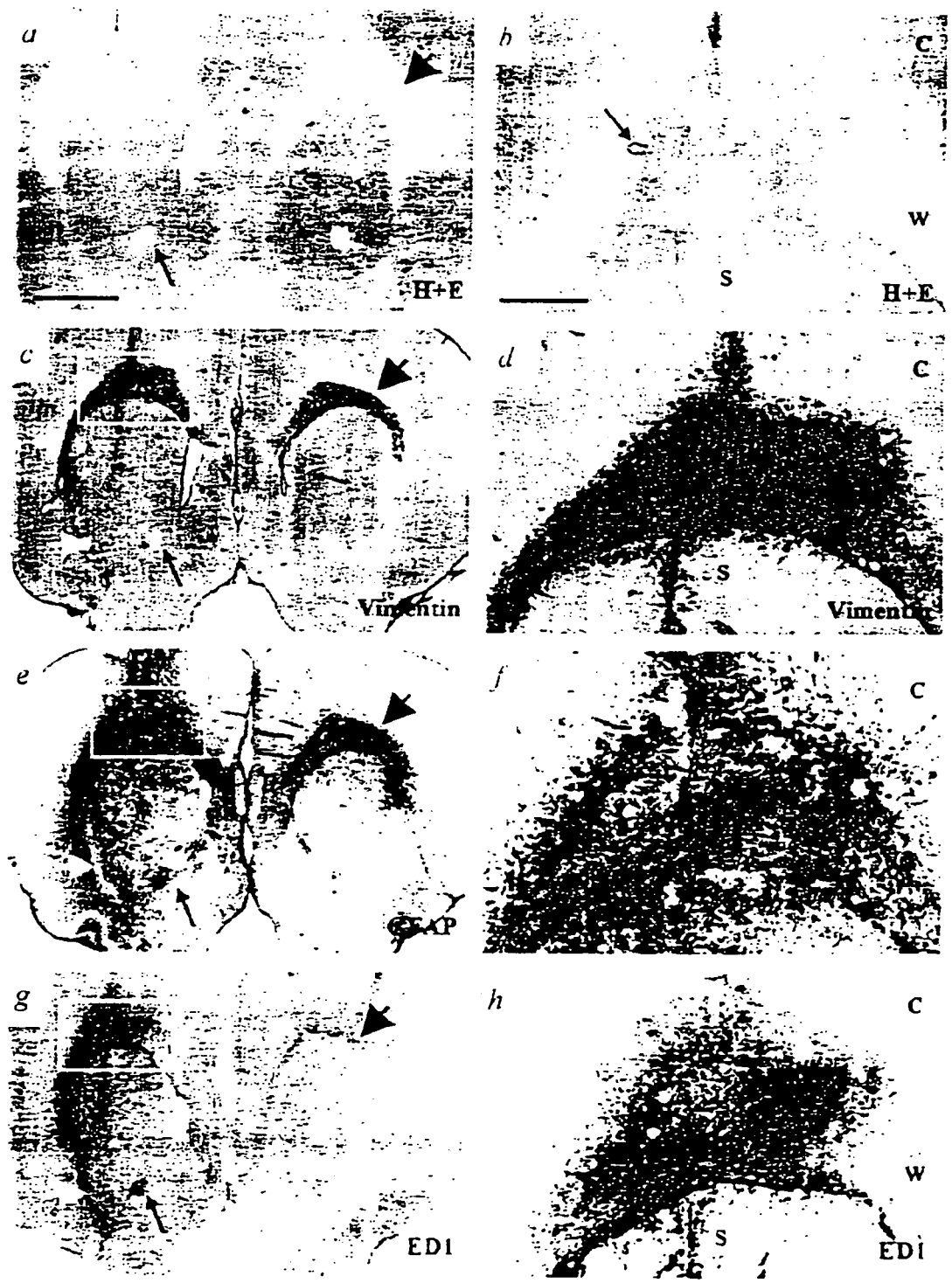
FIG. 2 shows brain inflammation in long-term suicide-gene therapy survivors. Abbreviations used in b, d, f, h are: (c) cortex, (w) white matter, (s) striatum.
Figure 3:
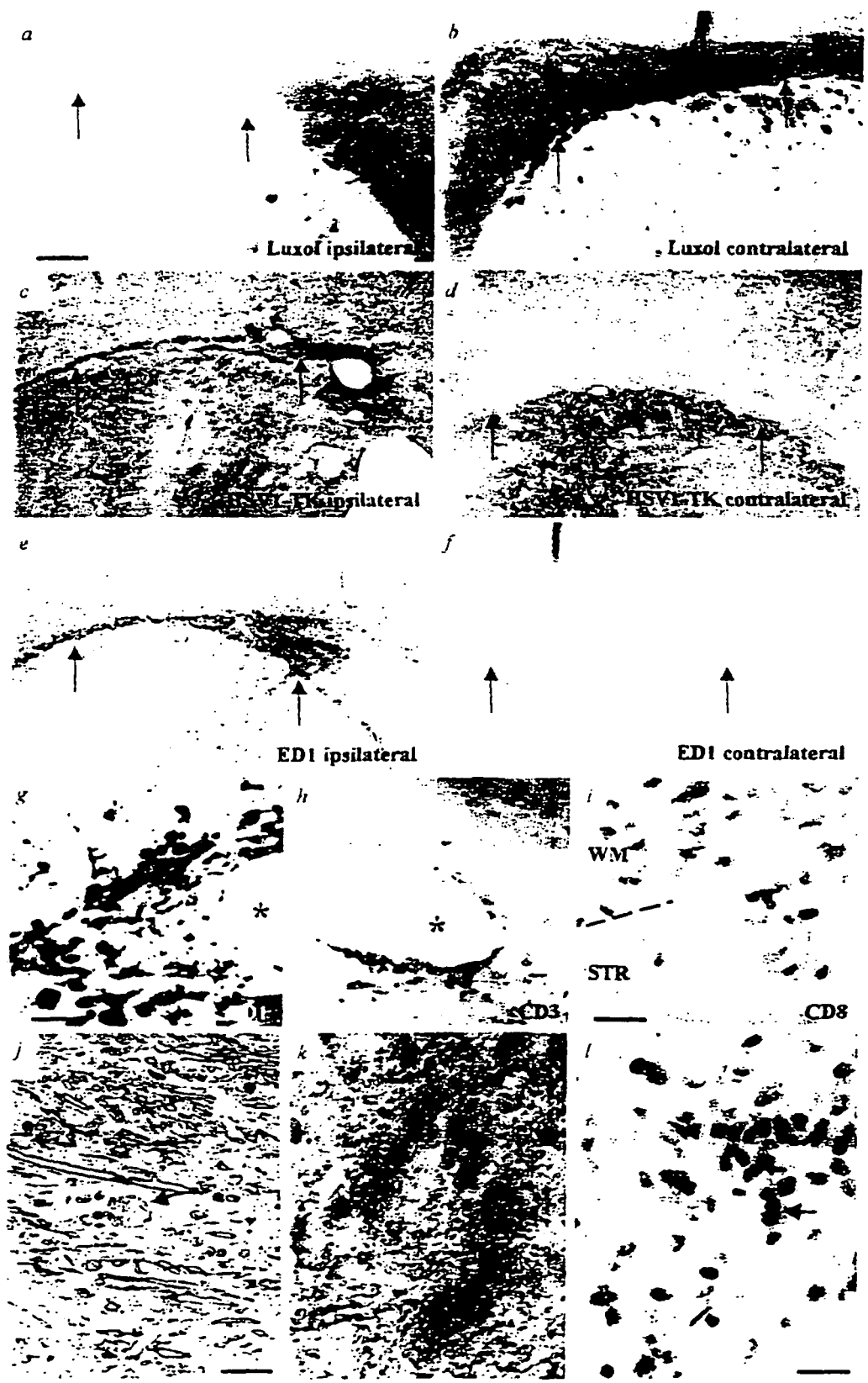
FIG. 3 shows loss of myelinated fibres, HSV1-TK immunoreactivity and macrophage and lymphocyte infiltration of perivascular cuffs. The decrease in myelinated fibres in long term suicide-gene therapy survivors is not due to autoimmune destruction of oligodendrocytes. Scale bars for a-f is shown in (a) equals 350 μm; scale bar for g-h is shown in (g) equals 35 μm; scale bar for (i) equals 40 μm; scale bar for (j)=50 μm; and for (k, l)=30 μm. Abbreviations used in (i) are: (WM) white matter, (STR) striatum.

Microglial/macrophage activation and lymphocyte infiltration Activated ED1 immunoreactive macrophages/microglia, displaying ongoing phagocytosis (i.e. containing tissue debris), were found mainly ipsilaterally, over a more restricted area than that occupied by activated astrocytes (illustrated in FIG. 2g, h). Within the ipsilateral subcortical white matter, the area occupied by ED1+, CD3+, leucosyalin+, or CD8+ cells overlapped with the hypercellularity detected in the hematoxylin and eosin, GFAP or vimentin stained sections (FIG. 2). In the striatum, activated microglia/macrophages were found surrounding the needle track, and infiltrating trans-striatal white matter tracts. Activated microglia/macrophages were distributed throughout the dorsal and ventral subcortical white matter, the corpus callosum, and the ipsilateral anterior commissure. Only very few could be detected in the contralateral subcortical white matter (see FIG. 3 e, f). Activated microglial/macrophages were also found within perivascular cuffs (FIG. 3g), together with, leucosyalin+, CD3+ and CD8+ lymphocytes (FIG. 3h). Lymphocytes were also found within the ipsilateral subcortical white matter, as well as infiltrating striatal tissue (FIG. 3 i, l).

Loss of Myelinated Fibres

The loss of Luxol fast blue staining strongly suggested a substantial reduction of myelinated fibres in the ipsilateral subcortical white matter (FIGS. 3a-b), which spread into its ventral extension. Luxol fast blue staining in the injected striatum was weaker than in the contralateral side, suggesting actual loss of myelinated fibres also within the striatum. Examination of semithin Epon-embedded sections (FIG. 3j) stained with osmium and toluidine blue to highlight myelinated fibres, confirmed the loss of myelinated fibres within the subcortical white matter. This also indicated the presence of increased extracellular space (due to fibre loss and edema), and an increase in cellularity, composed mostly of astrocytes and oligodendrocytes (FIG. 3j-l). The reduced density of myelinated fibres, the presence of oligodendrocytes (identified using specific CNPase antibodies; illustrated in FIG. 3k), together with the absence of primary demyelinated axons, strongly suggests that the loss of myelin fibres is secondary to tissue degeneration, rather than due to primary immune-mediated demyelination. The presence of axonal spheroids (FIG. 3j) further suggests ongoing axonal degeneration.

Long-Term Presence of Immunoreactive HSV1-TK Transgene in the Brains of Rats

Figure 4:
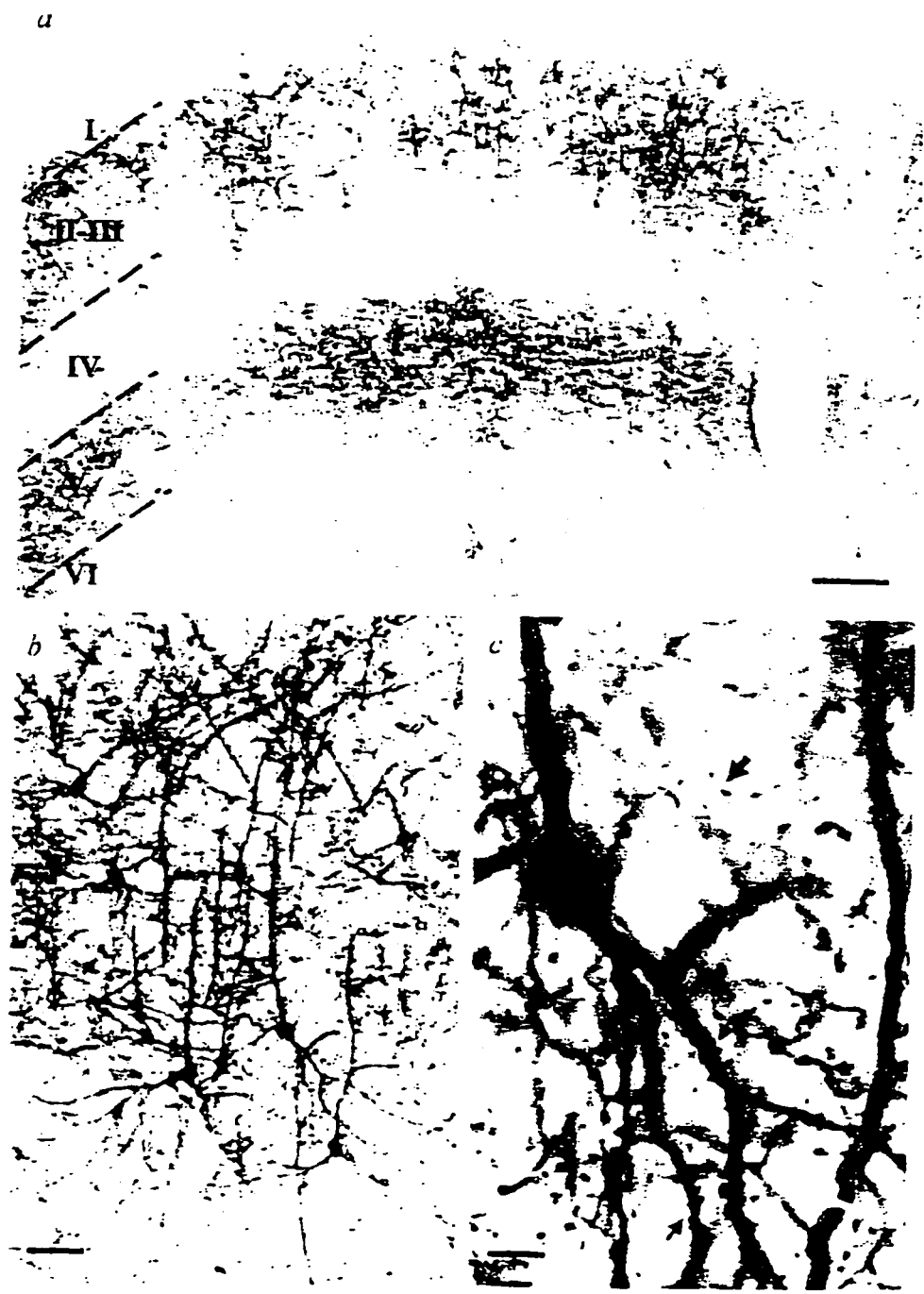
FIG. 4 shows persistence of HSV1-TK within neurones in long-term survivors of suicide-gene therapy. Small black arrows indicate the presence of labelling in dendritic spines, while the thicker arrow indicates labelled immuno-reactive axonal boutons. Scale bars: (a)=235 μm, (b)=50 μm, and (c)=10 μm.

We assessed the presence of HSV1-TK immunoreactivity in the brains of animals surviving tumour gene therapy for 3 months. Surprisingly, very strong and widespread immunoreactivity was detected (FIGS. 3c-d, FIG. 4, FIG. 5a). In the ipsilateral hemisphere, strong immunoreactivity was encountered in an area overlapping with the distribution of ED1+ microglia/macrophages within the subcortical white matter. Further, we detected strong HSV1-TK immunoreactivity throughout the ipsilateral striatum, both in neurons and axonal processes, as well as throughout the contralateral hemisphere (FIG. 4, 5a).

Large numbers of HSV1-TK immunoreactive neurons, axons, and synaptic boutons, were distributed throughout significant areas of the ipsilateral and contralateral cortex (FIGS. 3c, d: 4a-c: 5a). Immunoreactive neurons were mainly of pyramidal morphology, and were concentrated in layers II/III and V (FIGS. 4a-c). This strongly suggests that cortico-cortically projecting neurons contain high levels of HSV-1 TK protein. Importantly, brain areas displaying large numbers of strongly immunoreactive HSV1-TK neurons throughout the contralateral hemisphere (outside of the subcortical white matter), proved to be completely devoid of any ED1+ activated macrophages, or CD3/CD8 positive lymphocytes (see FIGS. 2g, 3e-f). Contralateral striata, only contained a large number of HSV1-TK immunoreactive axons (FIG. 3d, FIG. 5a). These most likely represent axons of cortical neurons projecting to lower levels of the neuraxis. Although strong labelling was found in all animals examined, the distribution of labelled cells varied between animals.

To exclude any non-specific immunoreactivity, the following controls were performed:

(i) Sections from animals injected with RAd-127 or RAd-128 and ganciclovir were immunoreacted with secondary antibodies in the absence of primary antibodies. No positive staining was observed, indicating that the secondary antibodies were not cross-reacting with non-specific tissue components.

(ii) Sections from animals treated with RAd35 and ganciclovir, or vehicle and ganciclovir were immunoreacted with primary anti-HSV1-TK and secondary antibodies. No immunopositivity was observed. This excludes the possibility that virus and/or ganciclovir injection might induce the production of an endogenous protein detected by anti-HSV1-TK antibodies.

Figure 5:
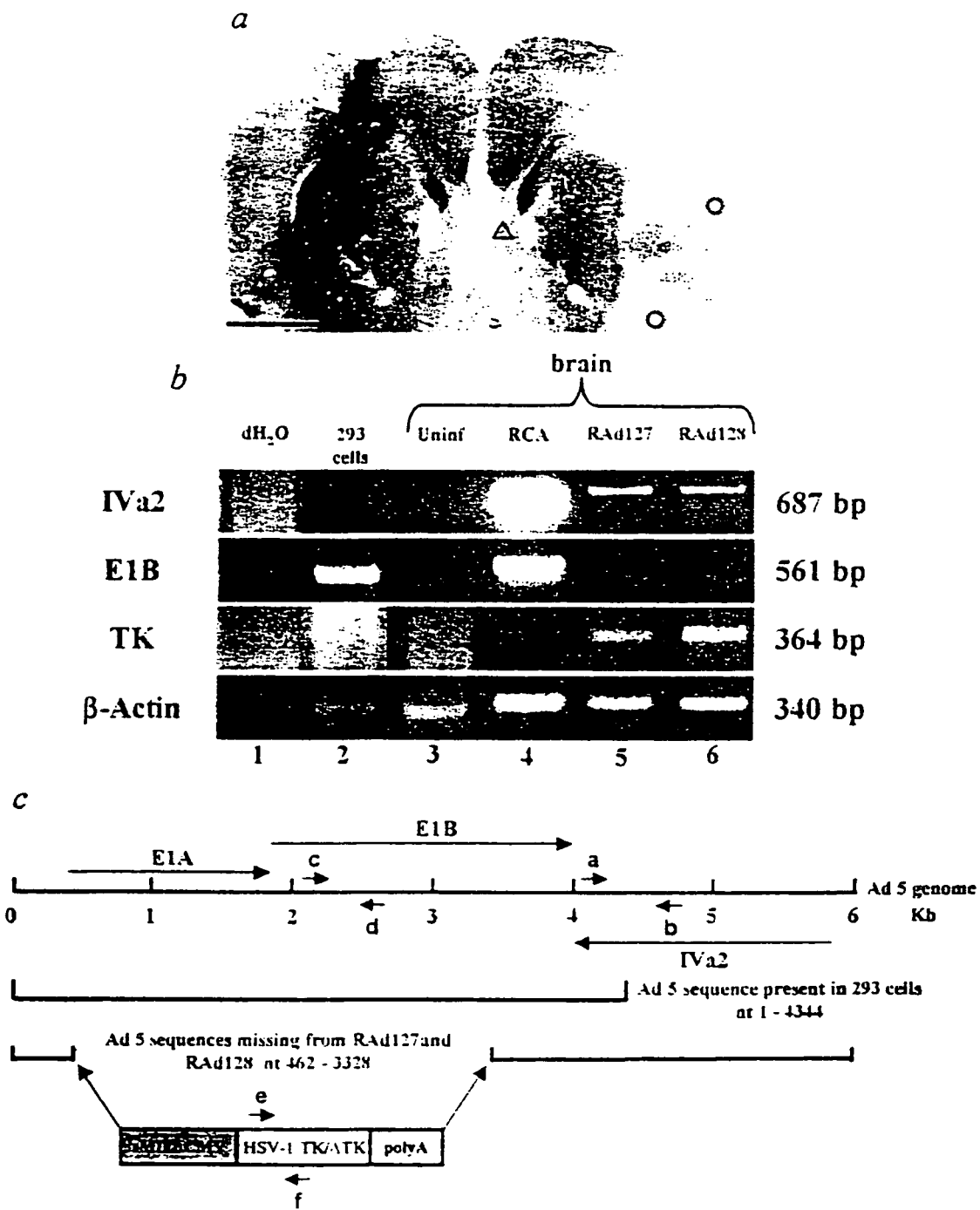
FIG. 5 shows PCR analysis of brain sections from long term suicide-gene therapy survivors. Immunohistochemical staining for HSV-1 TK in a 3 months survivor is shown in a coronal section in (a). The results of the PCR detection of vector genome (IVa2), transgene (TK), or replication competent genome (E1B), in brain sections of Rad128 and Rad127 treated animals, and which survived for 90 days is shown in (b). A schematic representation of the regions amplified by PCR is shown in (c). The sites of amplification for primer pairs a/b, c/d and e/f are indicated. Scale bar (a)=2 mm.

Also, viral stocks were tested prior to injection using the supernatant rescue assay and were shown to be devoid of replication competent adenovirus. To confirm that no very low level contamination could have been amplified in the brain during the three months of the experiment, a PCR based method was devised to detect the presence of any replication competent virus in the brain. Three regions of the viral genome were amplified by PCR from the same brain sections used for immunohistochemistry (FIG. 5 b, c). The IVa2 region is present in the genome of vectors, and in the genome of any replication competent virus. The E1B region is present in the genome of a replication competent virus, and in 293 cells, but not in the E1 deleted vectors. TK sequences will be present only in RAd127 and RAd128, and a β-actin sequence was used as a control for DNA extraction.

We amplified the TK and the IVa2 region, but not the E1B fragment, from sections of brains injected with either viral vector 3 months earlier (FIG. 5b). This demonstrates that vector genomes, but not replication competent viral genomes, were present. To confirm that the E1B fragment, if present, could be amplified from brain tissue, a preparation of an unrelated viral vector contaminated with replication competent adenovirus (as assessed using the supernatant rescue assay) was injected into the brain. From sections taken from such brains we amplified both the IVa2 and the E1B region, as expected (FIG. 5b).

Persistent Lymphocyte Infiltration is Not Seen following Immune-Mediated Elimination of CNS-1 Glioma Cells, but does Occur Following the Injection of RAd128 and Ganciclovir Treatment.

Figure 6:
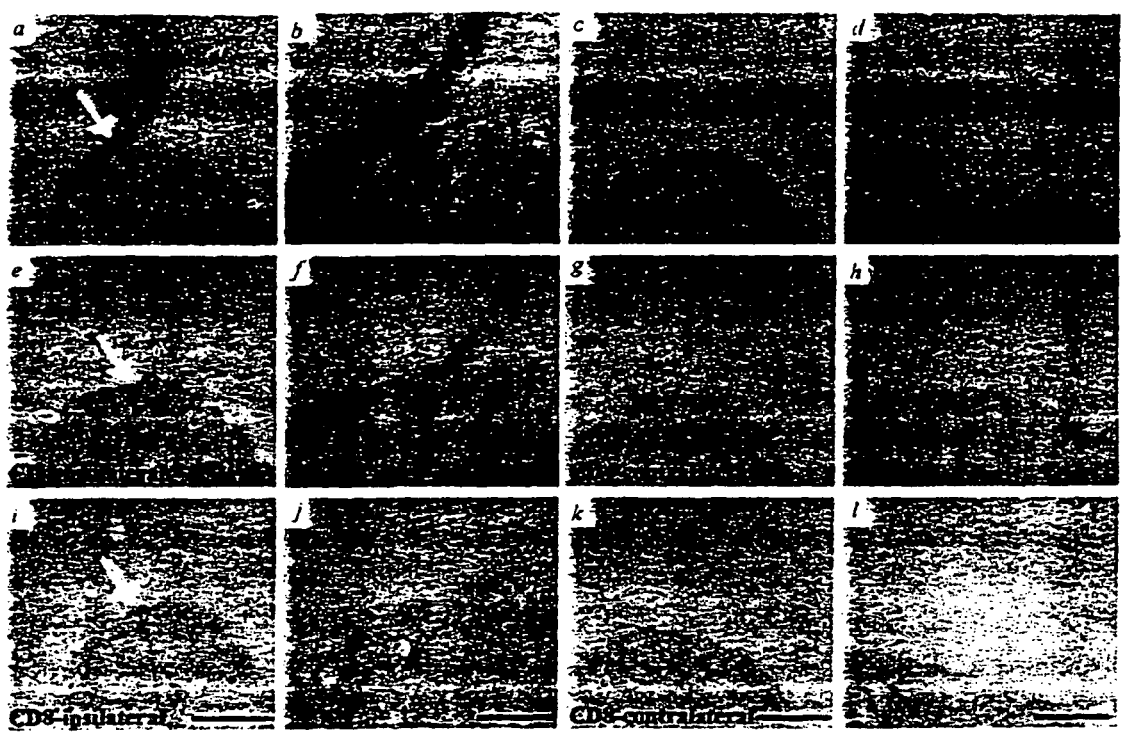
FIG. 6 shows immune-mediated elimination of CNS-1 cells does not lead to chronic persistent infiltration of CD4+ or CD8+ T-cells. Sections were photographed at a low magnification (a, e, i, c, g, k), and at higher magnification (b, f, j, d, h, l). Scale bars for a, e, i, c, g, k shown in (i,k)=1 mm and for b, f, j, d, h, l shown in, (j, l)=0.5 mm.
Figure 7:
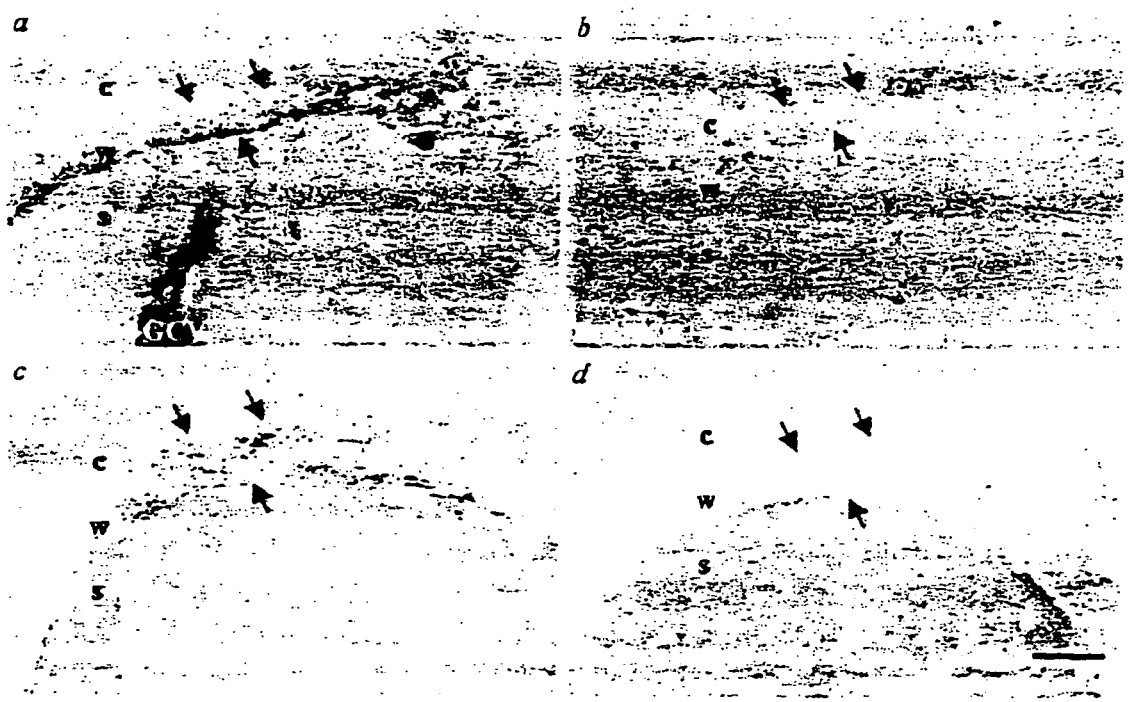
FIG. 7 shows that injection of RAd-125 followed by ganciclovir leads to chronic sustained infiltration of CD8+ T-cells. Arrows indicate the boundaries of the white matter showing T-cell infiltration. Abbreviations used in a-d are: (c) cortex, (w) white matter, (s) striatum. Scale bar for a-d, shown in (d)=450 μm.

To determine whether the chronic lymphocyte infiltration and inflammation was caused by (a) the elimination of CNS-1 cells, (b) the administration of viral vectors expressing HSV1-TK, or (c) the subsequent administration of GCV, these variables were tested independently. Peripheral priming of Lewis rats with 25,000 mitomycin-C treated CNS-1 cells, protected rats from a lethal intracerebral challenge with 5,000 CNS-1 cells. Surviving rats were perfusion-fixed 90 days following the intracerebral challenge. No tumour, CD8+, or CD4+, cells could be detected (FIG. 6). Only a modest increase of ED1+ macrophages/microglial cells was detected, compared to that following the inhibition of tumour growth by gene therapy (compare FIG. 6 a, b with FIG. 2 g, h). Thus, immune-mediated elimination of CNS-1 cells does not lead to a prolonged infiltration of lymphocytes into the brain. Intracerebral injection of $8 \times 10^7$ IU of RAd-128 in the absence of CNS-1 cells, followed by administration of ganciclovir or saline for 7 days, and perfusion-fixation 1 or 3 months later, led to a chronic brain inflammatory infiltration, with higher numbers of CD8+ lymphocytes in animals treated with ganciclovir (FIG. 7).

Long Term Transgene Expression using RAd-128 Encoding the Herpes Simplex Virus Type 1 Thymidine Kinase Gene Under the Control of a Short Powerful Immediate Early CMV Promoter.

Animals were injected with $1 \times 10^8$ infectious units (iu) of RAd-128, and either injected with ganciclovir or saline twice daily for 7 days. Groups of animals were then perfused 1 month, 3 months, 5 months, or 12 months later. Animals were perfusion-fixed and brains were cut in serial sections.

Figure 8:
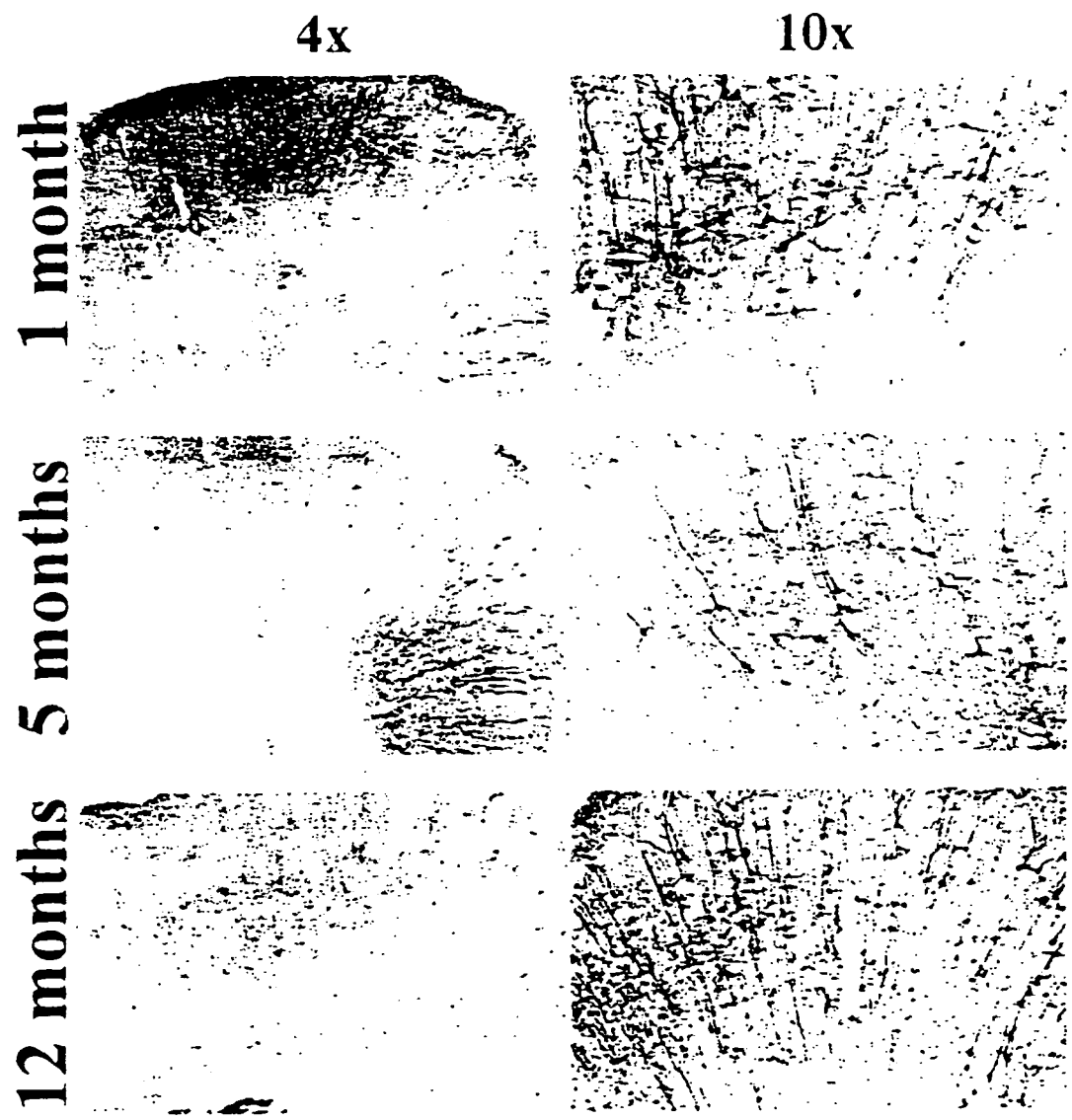
FIG. 8 shows persistence of HSV1-TK within neurons 1, 5 and 12 months following injection of adenovirus TK.

Immunostaining with antibodies against HSV1-TK showed very widespread distribution of immunoreactive neurons, which were found throughout the striatum, cortex, and even distant sites such as the substantia nigra (FIG. 8). It is important to notice that not only were neurons labelled on the ipsilateral side, but also on the contralateral side of the brain. This wide distribution has never been reported with any other transgene encoded by either adenoviral vectors, or any other viral vector.

TABLE 1

Expression and distribution of transgenes acutely and long term following the injection of RAd-HSV1-TK or RAd-βgal into the brains of rodents

|  | RAd-HSV1-TK | RAd-βgal |
| --- | --- | --- |
| Striatum | +++++ | ++ |
| Distant cortical sites | +++++ | − |
| Distant subcortical sites | +++++ | − |
| Longevity of expression | +++++ | + |

The results shown in the above table indicate that following the injection of RAd-HSV1-TK expression of transgene is very widespread and long term. Following injection of RAd-⊖gal, transgene expression is only seen in the striatum, and only very little can be detected long term.

Discussion

Three main findings were made in the course of our conditional cytotoxic gene therapy studies in a syngeneic rat glioblastoma model: (i) complete tumour growth inhibition in the majority of animals; (ii) a chronic, ongoing, inflammatory process, characterised by T-cell and macrophage/microglial infiltration and activation, and loss of myelinated fibres and axons in long-term survivors; and, (iii) transgenic HSV1-TK was still being expressed at very high levels in neurons throughout the brains of survivors ninety days post vector administration.

This is the first report of: (i) chronic active inflammation in response to a single, successful, brain glioma gene therapy regime; and, (ii) the long term presence of the therapeutic enzyme, HSV1-TK. Furthermore, we demonstrate that the chronic inflammatory process does not impair long-term transgene expression in the brain. As the presence of HSV1-TK throughout the contralateral cortex and striatum did not result in overt local inflammatory responses, additional mechanisms will have to be invoked to explain the usual short lived transgene expression following adenovirus vector-mediated gene transfer to the brain[18-21, 23-24].

Long-Term Striatal and Peri-Striatal Inflammatory Responses to the Treatment of Syngeneic Gliomas Most previous experimental models of glioblastoma gene therapy have used C6, 9L, or F98 glioma cells8-17, and failed to report any chronic inflammatory responses. Following a single administration of adenovirus encoding the marker gene β-galactosidase or HSV1-TK to either rats, mice, non-human primates, or human glioma, mainly acute, short-lived, and dose-dependent, inflammatory responses have so far been described[18-21, 23,24, 29-31]. The ongoing nature of the inflammatory process detected in our model is supported by our finding of perivascular cuffs, composed of both T-cells and activated microglia/macrophages. Importantly, injection volumes, viral and ganciclovir doses, and our experimental paradigm, are within the range described in the literature[8-17]. However, this is the first report of a syngeneic glioma gene therapy model in Lewis rats, which are highly susceptible to experimental allergic encephalomyelitis[32].

Previously, localised demyelination has only been described following the peripheral readministration of adenovirus vectors[19]. Moreover, in our experiments, the chronic inflammatory response was also limited to the hemisphere originally injected with tumour cells and viruses. Importantly, no inflammatory responses were detected at any distant sites expressing high levels of immunoreactive HSV1-TK. Further, our data uncovered a loss of myelinated fibres, edema, and indices of ongoing axonal degeneration, while oligodendrocytes were preserved and primary demyelinated axons absent. This demonstrates that the loss of myelinated fibres, is not primary, or immune-mediated, but secondary to tissue injury and axonal loss.

Adenovirus injection into brain parenchyma stimulates the secretion of IL-1 and IL-6, while injection into the lateral ventricle induces secretion of IL-1, IL-6, and TNF-$\alpha$[20]. Thus, the immune-suppressive microenvironment of the brain and gliomas (which express TGF-$\beta$[33] and Fas-Ligand[34]) could be modified by viral-mediated gene therapy, through the secretion of pro-inflammatory cytokines, coupled to inflammation elicited through HSV1-TK and ganciclovir mediated cell killing. This could enhance tumour immunogenicity and improve gene therapy's anti-tumour activity.

The persistent inflammation is not exclusively due to the elimination of CNS-1 cells, since the subcutaneous priming with growth arrested CNS-1 cells completely protected animals from an intracerebral challenge, without leading to a chronic inflammatory response. Thus, immune system-mediated elimination of glioma cells (as opposed to adenovirus mediated gene therapy) does not lead to chronic inflammation and lymphocyte infiltration. Importantly however, injection of RAd-128 followed by ganciclovir administration did cause an important influx of CD8+ cells, which was much reduced in the absence of ganciclovir treatment. Hence, the persistent inflammation is a result of the combined effect of HSV1-TK and ganciclovir, but is not a direct result of the elimination of the tumour cells per se. Whether this effect will be shown to be specific to adenovirally-encoded HSV1-TK, or whether it will be seen when HSV1-TK is expressed by other viral vectors remains to be determined.

Long-Term Presence of the Adenovirally Encoded HSV1-TK Transgene

Another significant finding was the widespread presence of immunoreactive HSV1-TK within ipsilateral and contralateral neocortex and striatum, as well as within ipsilateral glia and inflammatory cells 3 months following vector injection and ganciclovir administration. So, HSV1-TK immunoreactive cells either became infected following the administration of ganciclovir, or are resistant to HSV1-TK plus ganciclovir dependent cytotoxicity. HSV-1 immunoreactive neurons displayed normal morphologies, suggesting that the long-term presence of HSV1-TK and ganciclovir administration did not compromise neuronal survival. This contrasts with sympathetic neurons in culture, in which infection with adenovirus vectors led to neuronal death in a few days[35]. Our findings also contrast with previously published experiments describing much more anatomically restricted adenoviral encoded neuronal protein expression[18,19, 21-24].

The presence of HSV1-TK throughout the ipsilateral and contralateral neocortex was restricted to pyramidal neurons, mainly located in layers II-III and V, which contain callosally and cortico-cortically projecting pyamidal cells. Such neurons may have taken up vectors through axonal varicosities present on axons coursing throughout the subcortical white matter overlying the injected striatum[36]. Alternatively, HSV1-TK protein could have been released by dying cells (if spared from intracellular degradation) and taken up by axonal terminals to be transported retrogradely to parent neuronal cell bodies. This is unlikely, however, given the widespread distribution of HSV1-TK protein and viral vector genomes, in distant cells, including neurons, throughout the brain. The presence of vector genomes, but the absence of replication competent virus from brains of long term survivors, indicates the apparent stability of, and long term expression from, adenoviral vectors injected into the rodent brain.

Implications for Clinical Gene Therapy Trials of Glioblastoma Multiforme

In spite of aggressive surgery, chemo- and radiotherapy, median survival of glioblastoma patients is below 12-15 months, and has not improved during the last 30 years. This calls for novel treatments, such as gene therapy. All current treatments have significant side effects. Surgery can damage vital brain areas, chemotherapy has very high toxicity, and widespread demyelination is a long-term consequence of radiotherapy.

The above experiments appear to show the operation of two phenomena. One, is the enhanced distribution of transgene, which is not seen with any other transgene. The second one, is the very long term and distributed expression of the transgene throughout large areas of the brain. The basis underlying this phenomenon could be an intrinsic characteristic of the HSV1-TK gene, or the mRNA encoding HSV1-TK, or the protein itself. This intrinsic characteristic may be one found in all herpes virus genes. Further, it could be a characteristic of the gene that is dependent on the viral vector environment. It is possible that the widespread distribution and longevity of expression will be conferred onto any second gene co-expressed with a herpes virus gene, for example HSV1-TK, either in the same vector, or an associated vector that can infect the exact same cells simultaneously. These hypothesis are now being tested. It is further possible that the administration of ganciclovir confers an advantage, but how big this is, also remains to be determined.

Several clinical trials of glioblastoma suicide gene therapy using retro- and adenoviruses encoding HSV1-TK, in combination with ganciclovir, are currently ongoing[1-4]. Our work has several important implications for clinical trials of glioblastoma gene therapy using adenoviruses expressing HSV1-TK: (i) effective gene transfer may occur to so far unexpected widespread areas of the human brain; (ii) the development of a chronic inflammatory response in humans could lead to a loss of myelinated fibres; (iii) long term persistence of HSV1-TK could lead to improvements in the clinical trial's schedule of ganciclovir administration. Extending the administration of ganciclovir could improve the anti-tumour effect by allowing killing of transduced glioma cells that have not yet entered the cell cycle during short periods of post-surgical ganciclovir administration in current use. The severity of gene therapy's untoward effects will have to be balanced with its increased anti-glioblastoma efficiency, vis-a-vis the limitations of currently used therapies.

FURTHER EXAMPLES

Further studies to evaluate the spread, level, and longevity of RAd mediated HSV-1-derived-TK expression, driven by the MIE-hCMV promoter in the Lewis rat brain were carried out and described below. In particular the aim was to determine whether the high level and widespread expression of HSV-1-TK following the administration of an adenoviral vector into the brain seen in the earlier experiments described above was due to: (i) the ganciclovir treatment, (ii) tumour presence, or (iii) whether it was transgene dependent. These factors could not be dissected in the original experimental design.

In summary the results of these additional experiments demonstrate that, using the HSV-1 derived TK as a transgene:

1) Despite an inflammatory immune response, intra-striatal RAd mediated delivery leads to widespread, high-level and long lived neuronal transgene expression that is transgene dependent.
2) This effect does not depend on ganciclovir treatment of animals injected with the vector.
3) This effect is not dependent upon the co-implantation of potentially immune-suppressive glioma cells in the brain.
4) The effects detected are restricted to the RAd expressing HSV1-TK, since neither the spread, high level expression, nor widespread distribution are conferred upon a co-injected vector expressing a different transgene.

Harnessing this transgene dependent property could increase the spread and expression levels of therapeutic transgenes, thus improving their efficacy in the treatment of neurological disorders.

Materials and Methods

Vectors:

Experiment 1: Adenoviral vectors used were E1A deleted recombinant adenoviral vectors encoding the full length Herpes Simplex Virus-derived Thymidine Kinase gene[47] driven by the MIE-hCMV promoter, as described above.

Experiment 2: As experiment 1, in addition to a similar vector encoding lacZ (RAd 35) and a RAd encoding HPRT (RAd HPRT). Vectors were titrated by end point dilution, characterised by Southern blot or PCR and were negative for replication competent virus, as analysed by supernatant rescue assay, and lipopolysaccharide.

Experiment 1:

18 adult male Lewis rats (weight 250-300 g) had $5\times10^7$ infectious units (iu) of RAd 128 injected stereotactically into the mid striatum (co-ordinates: anterior to bregma +1 mm; lateral +3 mm; ventral −4 mm) whilst under halothane anaesthesia, using a 25-gauge needle on a 10 µl Hamilton syringe. 12 hours later, 9 rats received intra-peritoneal injections of ganciclovir 25 mg/kg twice daily and 9 received i.p. saline injections for 7 days. Four rats, 2 treated with GCV, and 2 injected with saline, were sacrificed by perfusion-fixation with Tyrode's solution containing 10 units/ml heparin (approx. 200 ml) followed by 250 ml of 4% paraformaldehyde in phosphate buffered saline (PBS) at 1 month, 3 months and 5 months. The remaining 6 rats (3 treated with ganciclovir, and three injected with saline) were sacrificed at 1 year.

Experiment 2:

To assess the effects of HSV-1 TK on the expression another transgene, lacZ, a combination of either RAd TK+RAd HPRT or RAd 35+RAd HPRT or RAd 35+RAd TK was injected into the mid striatum of 9 rats (3 rats per group). The total vector dose was $8\times10^7$ iu (i.e. $4\times10^7$ iu per vector).

Tissue Processing

Rat brains were post fixed overnight in 4% paraformaldehyde in PBS, then sectioned, using a Leica VT1000S vibrating blade microtome at 50 µm. Sections were stained by free-floating immunohistochemistry for HSV1-TK (rabbit polyclonal anti-HSV1-TK, courtesy of M. Janicot, Rhone Poulenc Rorer, Paris, France. Dilution 1:400), β-galactosidase (mouse monoclonal, Promega, dilution 1:1000), the macrophage marker ED1 (mouse monoclonal, Serotec, 1:1000 dilution) and cytotoxic T cell and NK cell marker CD8 (mouse monoclonal, Serotec, 1:500 dilution). Secondary antibodies used were biotinylated rabbit anti-mouse immunoglobulin or swine anti-rabbit immunoglobulin (Dako, Carpinteria, California, dilution 1:200).

Results

Spread of HSV1-TK

Figure 9:
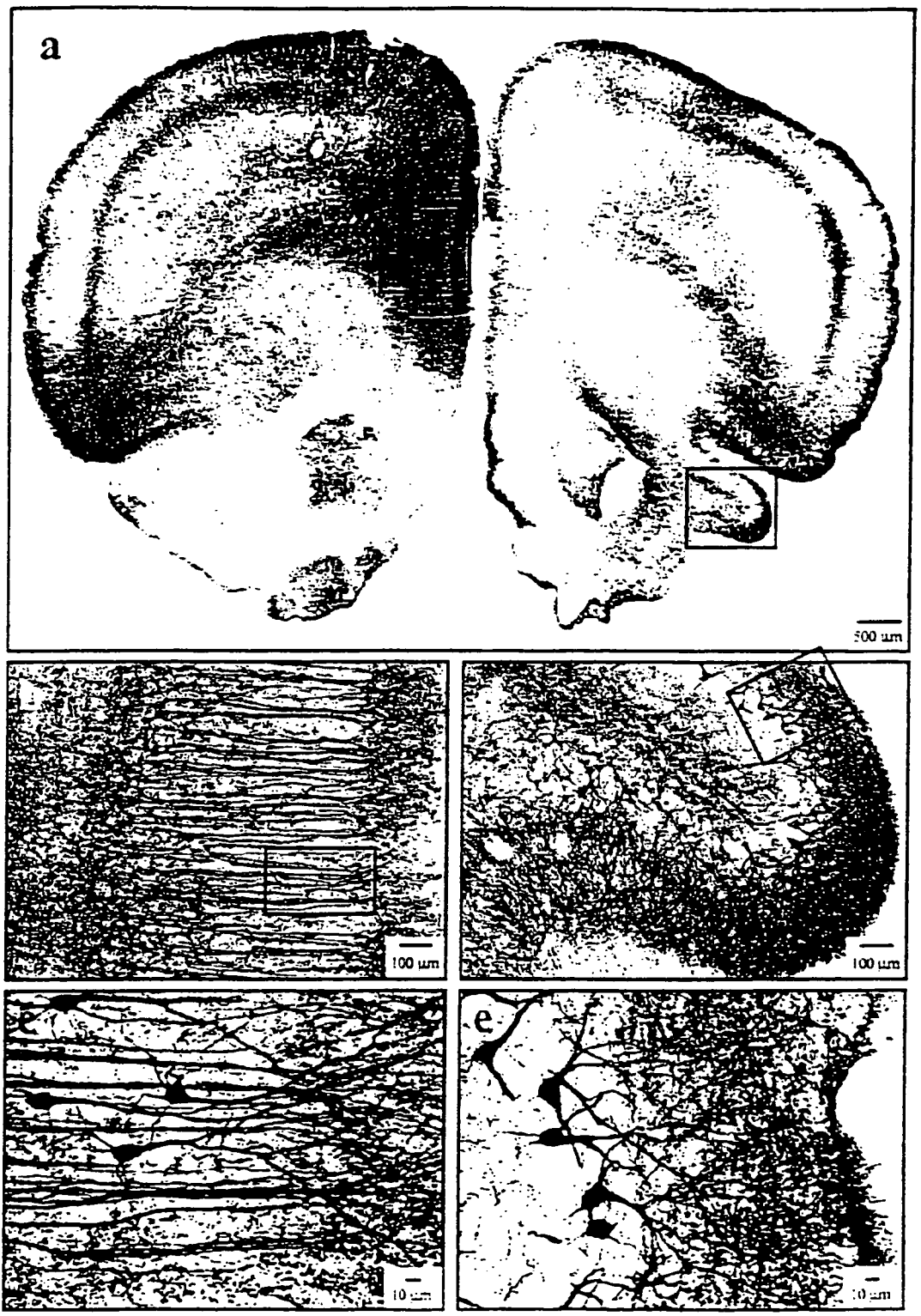
FIG. 9 shows widespread distribution HSV1-TK immunoreactivity throughout the anterior frontal and cingulate neocortex at 30 days post-vector injection, a: right side of this panel illustrates the hemisphere ipsilateral to the injection side, b shows boxed area of cingulate cortex at higher power, d shows boxed area of the piriform cortex at higher power, c and e are boxes enlarged from b and d respectively; notice the strong immunolabeling of pyramidal neurons, their dendrites as well as afferent and efferent axonal processes. Scale bars are shown in each of the panels.
Figure 10:
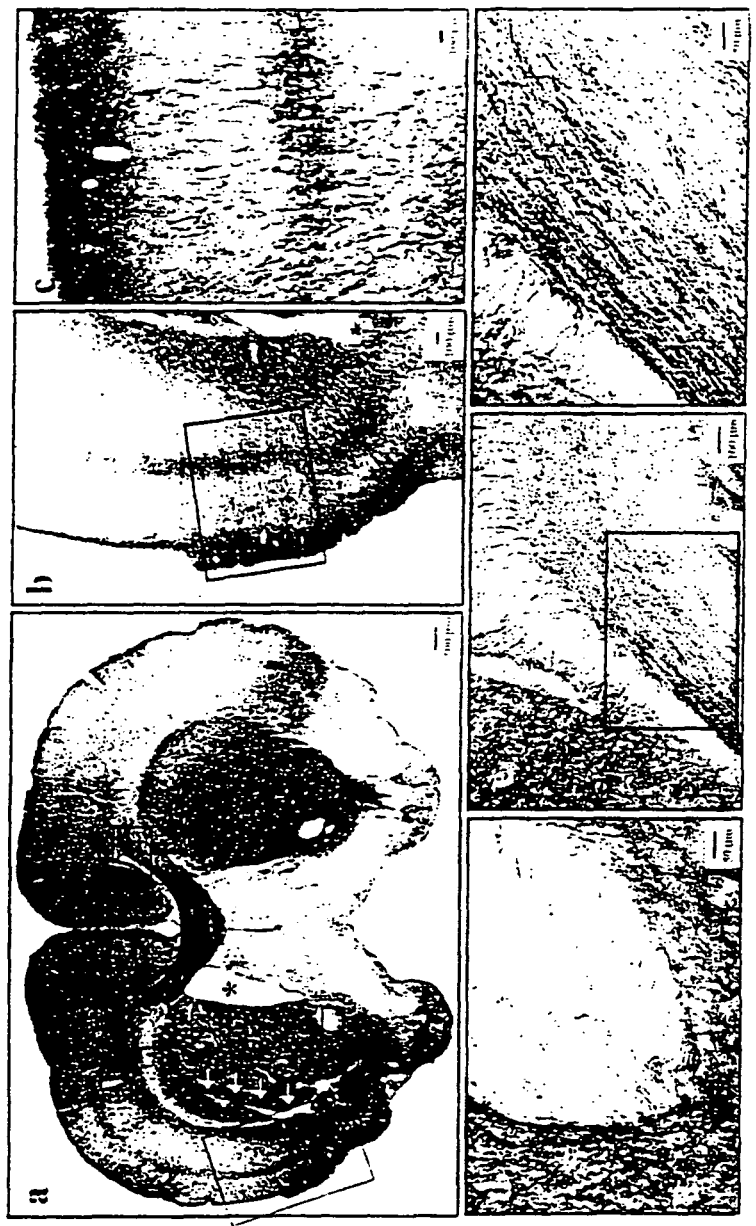
FIG. 10 shows widespread distribution HSV1-TK immunoreactivity at the level of the anterior striatum at 30 days post-vector injection. Arrows indicate the exact location of the original injection site. * indicates the enlarged lateral ventricle, ipsilateral to viral vector injection. Boxed areas in panel (a) are shown enlarged in (b) (insular cortex), (d) (anterior commissure) and (e) (corpus callosum). Box in (b), is shown enlarged in (c) to illustrate neuronal morphology. Box in (e), is shown enlarged in (f) to illustrate the detailed axonal morphology of axons coursing along white matter and entering or exiting the overlying cerebral cortex. Scale bars are shown in each of the panels.

FIGS. 9 and 10 show coronal brain sections at different anterior-posterior levels along the neuraxis, 1 month following a single intra-striatal injection of $5 \times 10^7$ i.u. of RAd HSV-1 TK. We detected a diffuse, high level HSV1-TK protein immunoreactivity throughout the striatum and many areas of the neocortex, both ipsilateral and contralateral to the injection site. In addition there was immunoreactivity in the anterior commissure, nucleus accumbens, ipsilateral nucleus of the horizontal limb of the diagonal band, magnocellular preoptic nucleus and several thalamic nuclei e.g. the paracentral, anteroventral and anteromedial thalamic nuclei (not shown), among others. FIG. 9 illustrates a difference in the distribution of HSV-1 TK immunoreactivity between the two hemispheres, and anterior levels of the neuraxis. Notice the lack of immunoreactivity in the olfactory cortical areas contralateral to the injection side. As opposed to the cingulate, frontal and parietal cortices, this area does not have axonal connections with the contralateral cortex or striatum, so vector could not reach this area through axonal pathways. Neurons, as well as their dendritic processes, axons, and axonal terminals could be clearly detected throughout both hemispheres. The decussating fibres of cortico-cortical axons, coursing through the corpus callosum could be clearly identified, and were seen branching off and entering the neocortex [FIG. 10].

Longevity of HSV1-TK Immunoreactivity

Figure 11:
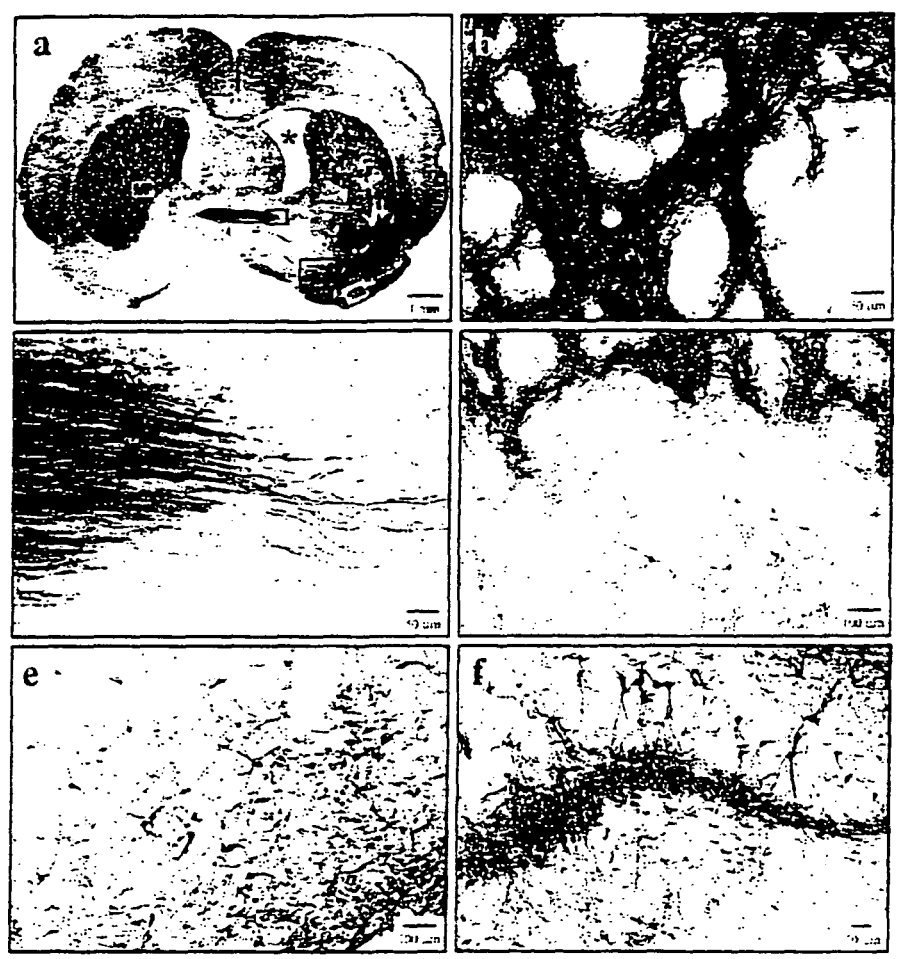
FIG. 11 shows a time-course of HSV-1 TK expression in rat neocortex at 1 month (a,d). 3 months (b,e) and 5 months (c,f). Rats illustrated in a-c received i.p. GCV and rats d-f received i.p. saline. Boxes to the right of each lettered panel show higher power views to illustrate neuronal morphology. Scale bar for the lettered (low power) panels is shown in (a), and the scale bar for all higher power views is shown to the panel to the right of (a).
Figure 12:
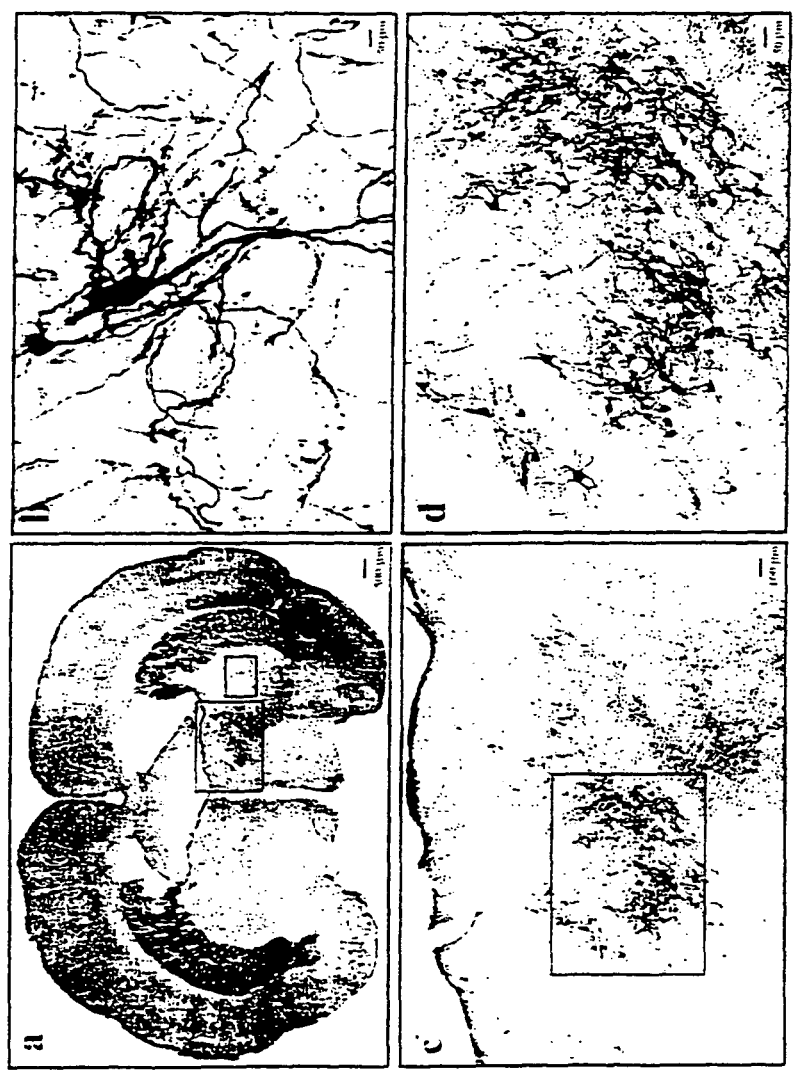
FIG. 12 shows sections from the neocortex of all 6 rats 1 year following the injection of adenovirus encoding HSV-1 TK. Panels shown in (a-c) illustrate the neocortex of rats treated with i.p. GCV; panels (d-e) illustrate the neocortex of rats treated with i.p. saline. Notice that there is individual variability in the HSV1-TK immunoreactivity detected. The highest level of immunoreactivity was detected in the animal illustrated in (d).

Cortical HSV1-TK immunoreactivity was maximal at 1 month post-vector administration and subsequently declined. FIGS. 11 and 12 show the brains displaying the strongest levels of immunoreactivity for each time point. Importantly, however, staining persisted even at 1 year post-vector injection in all 6 brains. HSV1-TK immunoreactivity in the brains of all animals sacrificed at 1 year are illustrated in FIG. 12. In one brain (FIG. 12d), cortical staining at 1 year was almost as high as at 1 month (FIG. 11). Striatal staining showed a similar maximum at 1 month and a gradual decline with persistence at 1 year (results not illustrated).

Although at 3 and 5 months there appeared to be more neocortical HSV1-TK immunoreactivity in the GCV treated group, this was not the case at either 1 month or 1 year. Indeed, at 1 year the highest level of immunoreactivity was detected in the brain of an animal injected with saline. Thus, we conclude that GCV had no effect on the maintenance of HSV1-TK immunoreactivity in the rodent brain. Furthermore, we did not detect any major differences in the degree of spread between the GCV and saline treated groups at any time point.

Co-Injection of RAd HSV-1 TK with RAd 35

Figure 13:
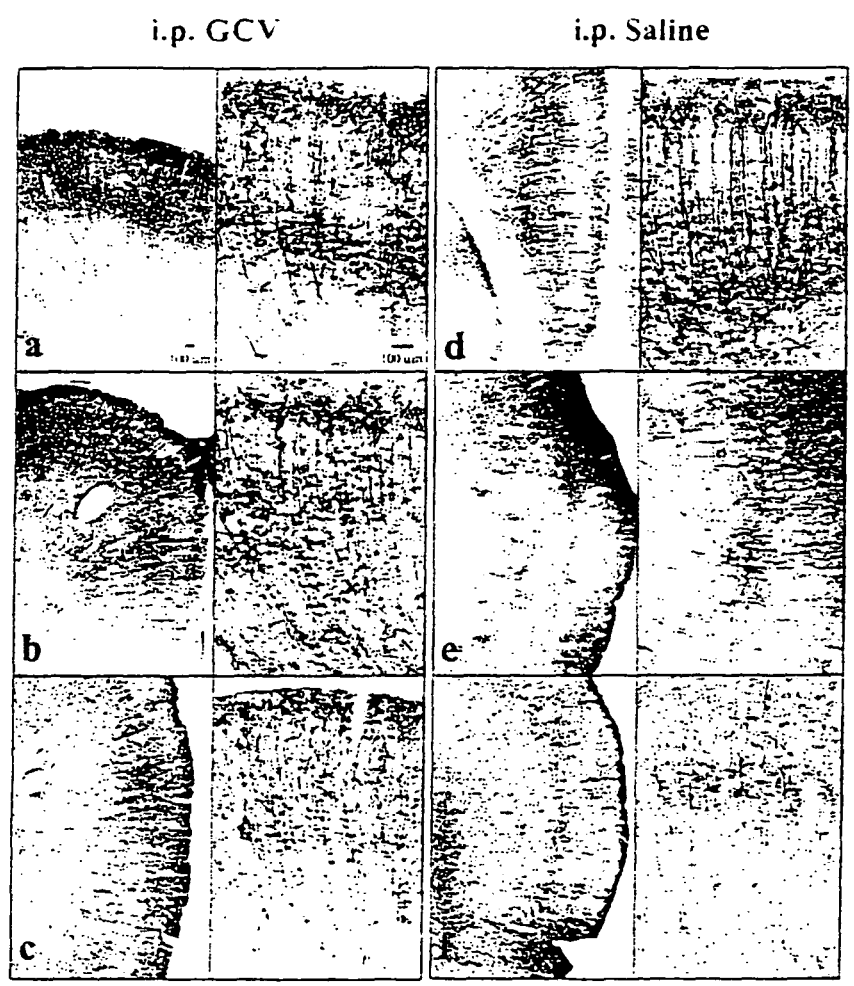
FIG. 13 shows co-injection of RAd HSV-TK with RAd β-Galactosidase. Panels shown in a-f illustrate sections taken from the same animal; panels a-c illustrate the forebrain and substantia nigra immunoreacted with β-galactosidase antibodies. Panels illustrated in d-f, are all serial sections to those shown in panels a-c, and were immunoreacted with antibodies against HSV-1 TK.

To investigate whether the above results were due to a property of the HSV1-TK protein potentiating transgene expression, RAd HSV1-TK was co-injected with RAd 35, a first generation adenoviral vector expressing the transgene lacZ, under the control of the exact same. MIEhCMV promoter [FIG. 13]. The striatal HSV1-TK immunoreactivity indicates that, from a technical point of view, the injection in these animals was successful in accuracy and delivery. Retrograde transport and expression is illustrated by the numerous HSV1-TK immunopositive neurons in the substantia nigra pars compacta, known to project to the corpus striatum. However, serial vibratome sections taken from the same site and immunoreacted for β-galactosidase, showed very little expression, limited to the area immediately around the needle tract of the corpus striatum with negligible retrograde expression in the substantia nigra pars compacta. A control with RAd 35 co-injected with RAd HPRT showed similar β-galactosidase expression.

Inflammatory Response

Figure 14:
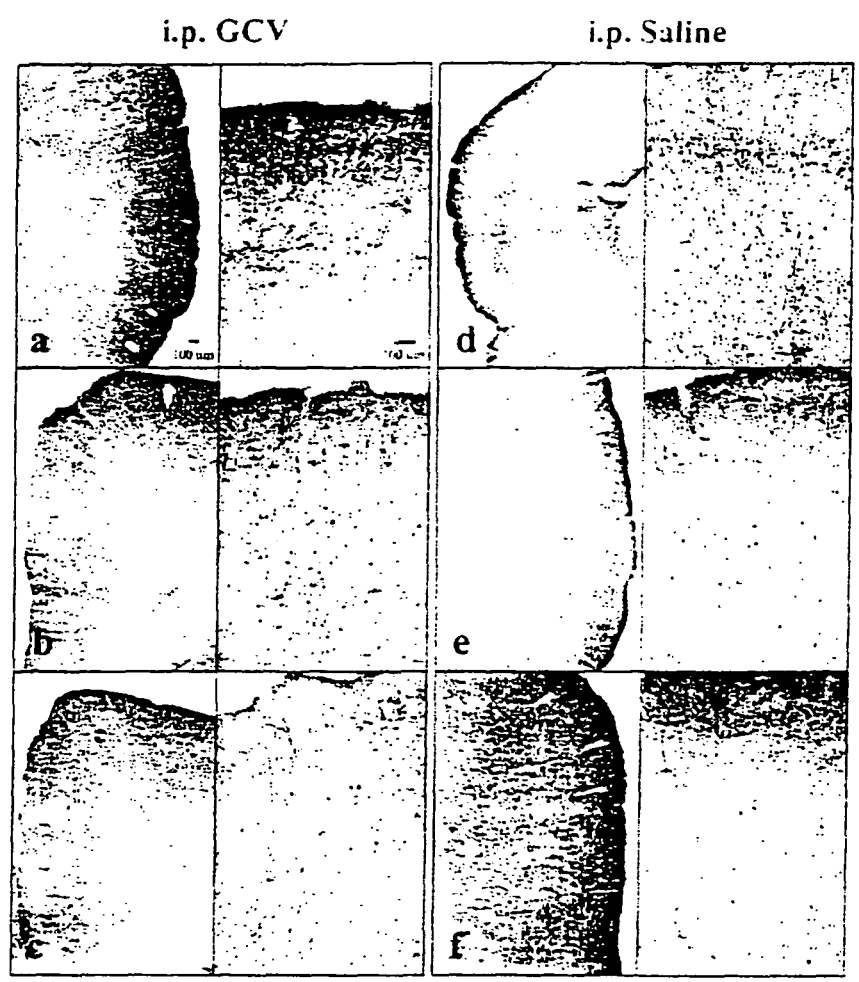
FIG. 14 shows inflammatory brain responses to the injection of RAd128 expressing HSV1-TK. ED1 staining of macrophages/microglial cells at 1 month (a,d), 3 months (b,e) and 5 months (c,f) post-vector injection is shown. Brains illustrated in a-c were obtained from animals which received i.p. GCV, while those shown in d-f received i.p.saline. CD8 staining is shown at 1 month (g,j), 3 months (h,k) and 5 months (i,l) post-vector injection; panels shown in g-i were obtained from animals which received i.p. GCV, and those illustrated in j-l received i.p.saline. Notice that inflammatory responses appear somewhat increased in those animals injected with ganciclovir.
Figure 15:
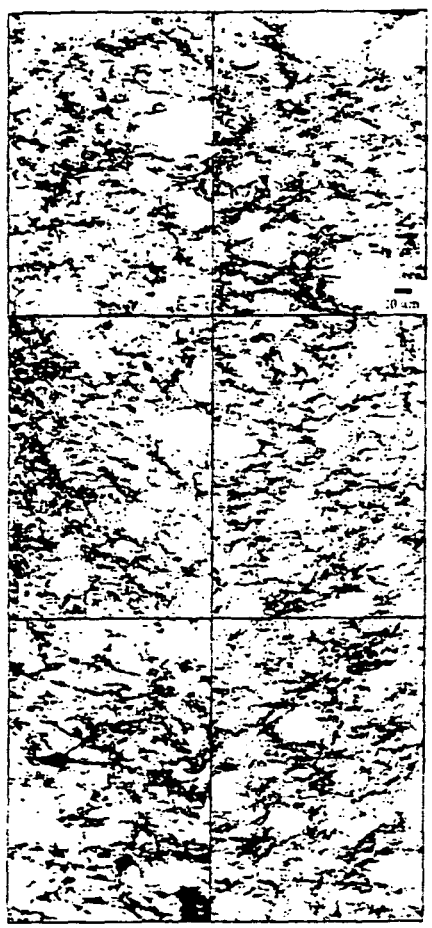
FIG. 15 shows immune response to RAd HSV1-TK in the brains of all 6 rats injected 1 year earlier with RAd128. Panels shown in a-f illustrate ED1 staining of macrophages/microglial cells: those in a-c received i.p. GCV, and those in d-f are from animals which received i.p.saline. Panels g-l illustrate CD3 staining: panels g-i are from animals that received i.p. GCV, and those shown in j-l are from animals which received i.p.saline. Arrow in g show mainly brownish coloured haemosiderin deposition.
Figure 15:
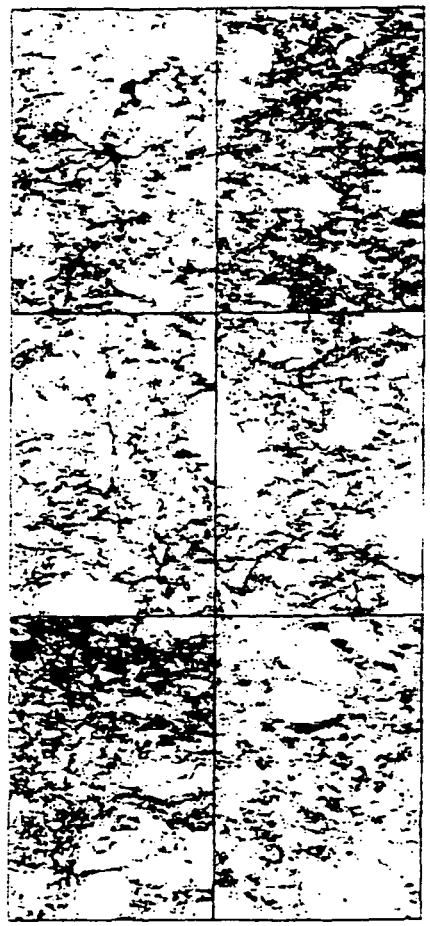
Figure 16:
FIG. 16: depicts co-injection of RAd128 (expressing HSV1-TK) with RAd35 (expressing β-galactosidase). Panels (A-F) show sections from the same animal; (A-B) forebrain, with (B) boxed area in (A) and ipsilateral substantia nigra (C), immunoreacted for β-galactosidase immunohistochemistry. (D-F) Serial sections to (A-C) were immunoreacted with antibodies to HSV1-TK; (E) boxed area in (D). Notice the presence of HSV1-TK (F), but not β-galactosidase (C) immunoreactivity in the ipsilateral substantia nigra. Also, notice the much higher level of HSV1-TK immunoreactivity throughout the striatum.
Figure 17:
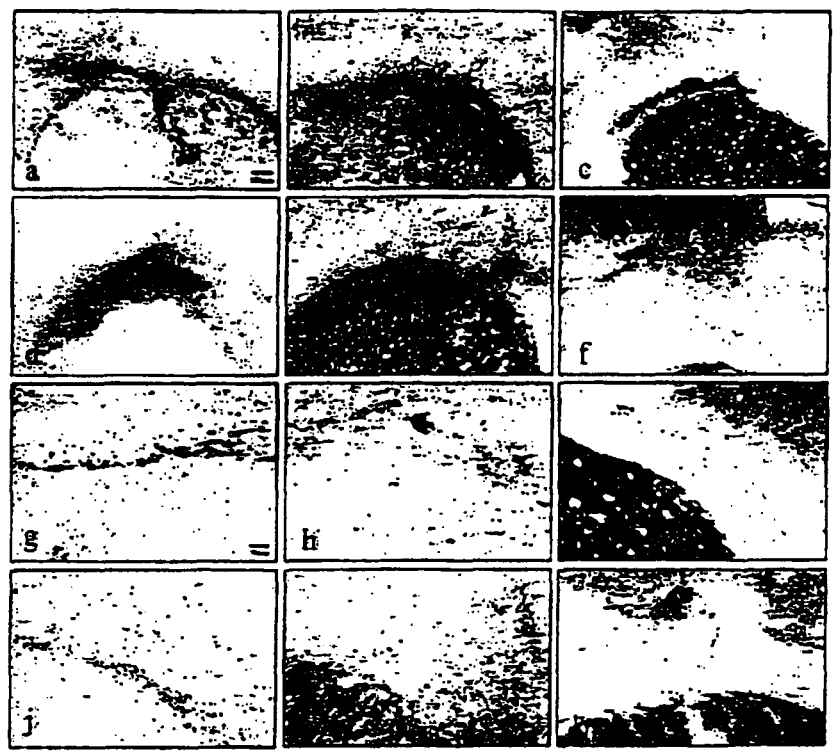
FIG. 17: depicts inflammatory brain responses following injection of RAd128 (HSV1-TK). ED1 immunohistochemistry of macrophages/microglial cells at 1 month (A, D), 3 months (B, E), and 5 months (C, F) post-injection is shown. Brains (A-C) were obtained from animals which received i.p. GCV, whereas (D-F) received i.p. saline. CD8 staining at 1 month (G, J), 3 months (H, K), and 5 months (I, L) post-injection is illustrated; panels (G-I) were from animals injected with i.p. GCV, and (J-L) from animals injected with i.p. saline.
Figure 18:
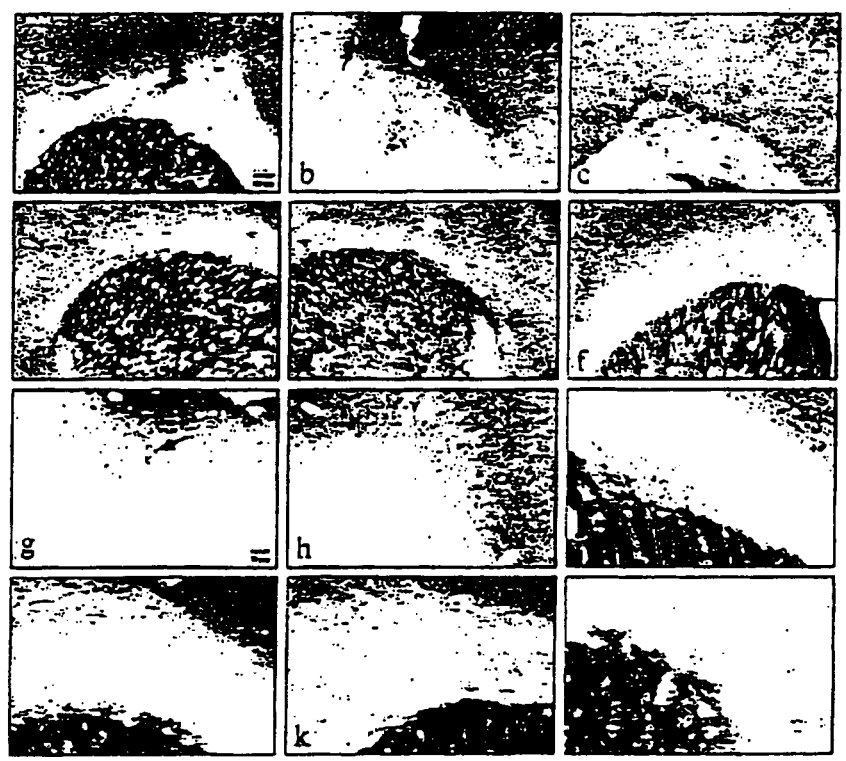
FIG. 18: depicts inflammatory brain responses to RAd128 in brains of six rats injected 1 year earlier with RAd128. (A-F) ED1 immunohistochemistry of macrophages/microglial cells. (A-C) received i.p. GCV, and (D-F) received i.p. saline. Panels (G-L) illustrate CD8 staining; (G-I) received i.p. GCV, and (J-L) received i.p. saline.

There was a strong initial immune response to the vector as illustrated by the ED1 (a macrophage and activated microglial marker) [FIGS. 14a-f] and CD8 (NK cell and cytotoxic T cell marker) [FIGS. 14g-h] immunoreactivity. Apart from the 1-year time point [illustrated in FIG. 15], all brains showed similar levels of inflammation, which gradually declined over the year. Despite widespread transgene expression, the ED1 and CD8 response was limited to the area of brain tissue surrounding the injection site. At 1 year, 5 of the brains showed similar levels of inflammation. Interestingly, one brain showed widespread ED1 staining [FIG. 15c] associated with enlargement of the ventricles and reduced striatal volume bilaterally. However, this was not accompanied by comparable CD8 persistence. Levels of inflammation detected at 1 and 3 months post-injection were similar to those reported previously.

Discussion

This paper illustrates the remarkable phenomenon of widespread, high level and long term HSV-1 TK expression in the brain when delivered by a first generation recombinant adenoviral vector. This phenomenon is not dependent upon the promoter or vector, but unexpectedly, the HSV1-TK transgene itself. It also illustrates the shortcomings of relying on gene expression as an indicator of the efficiency of adenovirus transduction of the brain: RAd-mediated expression of intracellular proteins would be judged much less efficient on the basis of most results described in the current literature.

This phenomenon can be explained by a combination of factors. Firstly, since RAds are known to undergo retrograde axonal transport, the pattern of staining is likely to due to this, as opposed to diffusion. A recent paper by Gerdes et al[48] showed that using the MIEmCMV promoter, much higher transgene expression levels could be achieved in the brain, following the injection of very low doses of viral vectors. However, although spread of transgene expression increased, it was still limited to the ipsilateral striatum. Since the MIEmCMV is a glial specific promoter, this was not totally unexpected. Even if virus spread to other parts of the brain by axonal transport, this could possibly not be detected using MIEmCMV driven transgene expression as a marker for viral spread. These data show, however, that adenovirus can diffuse in the brain over much larger distances than previously thought.

The most likely explanation that retrograde transport lead to the spread of RAd-encoded HSV1-TK throughout the brain is illustrated by the immunopositive axons seen in the corpus callosum, the main 'decussating highway' of the brain. Furthermore, the piriform cortex contralateral to the injection site was devoid of HSV1-TK immunoreactivity, while the ipsilateral piriform cortex did display strong HSV1-TK staining. Importantly, the piriform cortex is not connected by strong contralateral cortico-cortical or cortico-striatal connections. Retrograde transport of adenovirus has been described previously, but the extent detected in our experiments, was unexpected. Thus, there is either more expression and/or less clearance of the HSV1-TK protein or HSV1-mRNA. Apart from the transgene, the vector and expression cassette are the same as in our vector RAd35, which expresses β-gal. The difference between β-gal and HSV1-TK expression when co-injected excludes the possibility of altered anti-vector immune responses leading to such high levels and widespread HSV1-TK expression. However, it does not exclude the possibility that the HSV1-TK protein could be less immunogenic. However, this in unlikely since when tested side by side HSV1-TK was shown to be more inflammatory than β-gal.

The most likely explanation for the high levels of expression is that the HSV1-TK transgene is potentiating or stabilising its own expression levels above that dependent on the MIE-hCMV promoter. This is supported by two studies, which showed that the HSV-1 TK gene contains several short nucleotide sequences or sub-elements within its translated region that facilitate pre-mRNA transport from the nucleus to the cytoplasm. These sub-elements may also act by enhancing transcriptional activation, stabilising mRNA and enhancing translation. The mechanisms by which they function have yet to be fully elucidated. However, at least one of these 'RNA processing enhancers', an 119 nucleotide sequence isolated by Liu and Mertz, binds in a sequence specific manner to heterogeneous nuclear ribonucleoprotein (hnRNP) L, hnRNPs are a group of ribonucleoproteins which are known to be involved in the regulation of mRNA transport, turnover and translation.

The widespread transgene expression with HSV1-TK illustrates how important either vector and/or transcriptional targeting will be when using potentially cytotoxic transgenes in the CNS. On the other hand, harnessing this phenomenon will allow more widespread transgene expression in the treatment of global brain disorders.

REFERENCES

1. Izquierdo, M. et al. Human malignant brain tumour response to herpes simplex tymidine kinase (HSVtk)/ganciclovir gene therapy. Gene Therapy 3, 491-495 (1996).
2. Ram, Z. et al. Therapy of malignant brain tumors by intratumoral implantation of retroviral vector-producing cells. Nature Medicine 3, 1354-1361 (1997).
3. Klatzmann, D. et al. A phase I/II study of herpes simplex virus type 1 thymidine kinase "suicide" gene therapy for recurrent glioblastoma. Human Gene Therapy 9, 2595-2604 (1998).
4. Eck, S. L. et al. Treatment of advanced CNS malignancies with the recombinant adenovirus H5.010RSVTK: a phase I trial. Human Gene Therapy 7, 1465-1482 (1996).
5. Freeman. S. et al. The "bystander effect": tumour regression when a fraction of the tumour mass is genetically modified. Cancer Research 53, 5274-5283 (1993).
6. Freeman, S. M., Ramesh. R. and Marrogi, A. J. Immune system in suicide gene therapy. The Lancet 349, 2-3 (1997)
7. Gagandeep, S., Brew, R., Green, B., Christmas, S. E., Klatzmann, D., Poston, G. J., and Kinsella, A. R. Prodrug-activated gene therapy: involvement of an immunological component in the "bystander effect". Cancer Gene Therapy 3, 83-88 (1996).
8. Barba, D., Hardin, J., Sadelain. M. & Gage, F. Development of anti-tumor immunity following thymidine kinase-mediated killing of experimental brain tumors. Proceedings of the National Academy of Sciences, USA 91, 4348-4352 (1994).
9. Beck. C., Cayeux. S., Lupton. S. Dorken, B. & Blankenstein, T. The thymidine kinase/ganciclovir-mediated "suicide" effect is variable in different tumour cells. Human Gene Therapy 6, 1525-1530 (1995).
10. Chen, S.-H., Shine, H. D., Goodman, J., Grossman, R. & Woo, S. L. C. Gene therapy for brain tumors: regression of experimental gliomas by adenovirus-mediated gene transfer in vivo. Proceedings of the National Academy of Sciences. USA 91, 3054-3057 (1994).
11. Culver, K. et al. In vivo gene transfer with retroviral vector-producer cells for treatment of experimental brain tumors. Science 256, 1550-1552 (1992).
12. Ezzeddine, Z. et al. Selective killing of glioma cells in culture and in vivo by retrovirus transfer of the herpes simplex virus thymidine kinase gene. The New Biologist 3, 608-614 (1991).
13. Izquierdo, M. et al. Long-term rat survival after malignant brain tumor regression by retroviral gene therapy. Gene Therapy 2, 66-69 (1995).
14. Maron, A. et al. Gene therapy of rat C6 glioma using adenovirus-mediated transfer of the herpes simplex virus thymidine kinase gene: long-term follow-up by magnetic resonance imaging. Gene Therapy 3, 315-322 (1996).
15. Perez-Cruet, M. et al. Adenovirus-mediated gene therapy of experimental gliomas. Journal of Neuroscience Research 39, 506-511 (1994).
16. Ram, Z. et al. The effect of thymidine kinase transduction and ganciclovir therapy on tumor vasculature and growth of 9 L giomas in rats. Journal of Neurosurgery 81, 256-260 (1994).
17. Ambar, B. B. et al. Treatment of experimental glioma by administration of adenoviral vectors expressing Fas ligand. Human Gene Therapy 10, 1641-1648 (1999).
18. Byrnes, A. P., Rusby, J. E., Wood, M. J. A. and Charlton, H. M. Adenovirus gene transfer causes inflammation in the brain. Neuroscience 66, 1015-1024 (1995).
19. Byrnes, A. P., MacLaren, R. E., and Charlton, H. M. Immunological instability of persistent adenovirus vectors in the brain: peripheral exposure to vector leads to renewed inflammation, reduced gene expression, and demyelination. The Journal of Neuroscience 16, 3045-3055 (1996).
20. Cartmell, T., Southgate, T., Poole, S., Castro, M. G., Lowenstein, P. R. and Luheshi, G. N. L-1 mediates a rapid inflammatory response following adenoviral vector delivery into the brain. The Journal of Neuroscience, 19, 1517-1523 (1999).
21. Geddes, B. J., Harding, T. C., Lightman, S. L. & Uney, J. B. Long-term gene therapy in the CNS: reversal of hypothalamic diabetes insipidus in the Brattleboro rat by using an adenovirus expressing arginine vasopressin. Nature Medicine 3, 1402-1404 (1997).
22. Ghodsi, A. et al. Extensive $\beta$-glucuronidase activity in murine central nervous system after adenovirus-mediated gene transfer to brain. Human Gene Therapy 9, 2331-2340 (1998).
23. Blomer U, Naldini L, Kafri T, Trono D, Verma I M & Gage F H Highly efficient and sustained gene transfer in adult neurons with a lentivirus vector. J. Virol 71, 6641-9 (1997).
24. Hermens W T & Verhaagen J Suppression of inflammation by dexamethasone prolongs adenoviral vector-mediated transgene expression in the facial nucleus of the rat. Brain Res Bull 47, 133-40 (1998).
25. Kruse C A, Molleston M C, Parks E P, Schiltz P M, Kleinschmidt-DeMasters B K & Hickey W F. A rat glioma model, CNS-1, with invasive characteristics similar to those of human gliomas: a comparison to 9 L gliosarcoma. Journal of Neurooncology 22, 191-200 (1994).
26. Salomon, B et al. A truncated herpes simplex virus thymidine kinase phosphorylates thymidine and nucleoside analogs and does not cause sterility in transgenic mice. Molecular and Cellular Biology 15, 5322-5328 (1995).
27. Dewey, R. A., Southgate, T., Morelli, A., Klatzmann, D., Castro, M. G. and Lowenstein, P. R. Adenoviral-mediated suicide gene therapy using the CNS-1 rat glioma model. Abstracts Society for Neuroscience, Part 2, 2165, No. 859.9 (1998).
28. Dewey, R. A. Rowe, J Southgate, T. D., Morelli, A., Forrest, Z., Klatzmann, D., Wilkinson, G. W. G. Lowenstein P. R. and Castro, M. G. Efficient conditional cytotox- 28. icity in neuroblastoma cells, and reduced non-specific toxicity in vitro and in vivo of a truncated variant of the herpes simplex virus type 1 thymidine kinase, expressed by recombinant adenoviruses. Gene Therapy, 1999 (Under review).
29. Goodman, J. et al. Adenoviral-mediated thymidine kinase gene transfer into the primate brain followed by systemic ganciclovir: pathologic, radiologic, and molecular studies. Human Gene Therapy 7, 1241-1250 (1996).
30. Smith. J. et al. Intracranial administration of adenovirus expressing HSV-TK in combination with ganciclovir produces a dose-dependent, self-limiting inflammatory response. Human Gene Therapy 8. 943-954 (1997).
31. Puumalainen, A. et al. Beta-galactosidase gene transfer to human malignant glioma in vivo using replication-deficient retroviruses and adenoviruses. Human Gene Therapy 9, 1769-74 (1998).
32. Klinkert W E, Kojima K, Lesslauer W, Rinner W, Lassmann H & Wekerle H TNF-alpha receptor fusion protein prevents experimental auto-immune encephalomyelitis and demyelination in Lewis rats: an overview. Journal of Neuroimmunology 72, 163-168 (1997).
33. Weller M & Fontana A. The failure of current immunotherapy for malignant glioma. Tumor-derived TGF-beta, T-cell apoptosis, and the immune privilege of the brain. Brain Res Brain Res Rev 21, 128-51 (1995).
34. Gratas et al. Fas ligand expression in glioblastoma cell lines and primary astrocytic brain tumours. Brain Pathology 7, 863-869 (1997).
35. Easton R M, Johnson E M & Creedon D J. Analysis of events leading to neuronal death after infection with E1-deficient adenoviral vectors. Mol Cell Neurosci 11, 334-47 (1998).
36. Shering, A. F. & Lowenstein, P. R. Neocortex provides direct synaptic input to interstitial neurons of the intermediate zone of kittens and white matter of cats: a light and electron microscopic study. The Journal of Comparative Neurology 347: 433-443 (1994).
37. Morelli, A., Larregina, A., Smith, J., Dewey, R., Southgate, T., Fontana. A., Castro M. G. and Lowenstein, P. R. Reduced systemic toxicity of recombinant adenovirus vectors expressing the Apoptotic molecule Fas-L driven by cell-type specific promoters. Journal of General Virology, 1999 80: 571-583.
38. Shering, A. F., Bain, D., Stewart, K. S., Epstein, A. L., Castro, M. G., Wilkinson, G. W. G. and Lowenstein. P. R. Cell-type specific expression in brain cell cultures from a short human cytomegalovirus major immediate early promoter depends on whether it is inserted into herpesvirus or adenovirus vectors. Journal of General Virology. 78: 445-459 (1997).
39. Cotten, M., Baker, A., Saltik. M., Wagner, E. & Buschle, M. Lipopopysaccharide is a frequent contamination of plasmid DNA preparations and can be toxic to primary human cells in the presence of adenovirus. Gene Ther. 1:239-246 (1994).
40. Hauss-Wgrzyniak, B., Lukovic, L., Bigaud, M. & Stoeckel, M. E. Brain inflammatory response induced by intracerebroventricular infusion of lipopolysaccharide: an immunohistochemical study. Brain Research 794, 211-224 (1998).
41. Dion, D. L., Fang, J. & Garver Jr., R. I. Supernatant rescue assay vs. polymerase chain reaction for detection of wild type adenovirus-contaminating recombinant adenovirus stocks. Journal of Virological Methods 56:99-107 (1996).
42. Lowenstein, P. R., Shering, A. F., James, J. L., Cohen, P. & McDougall, L. The distribution of protein phosphatase inhibitor, Inhibitor 1, in the neocortex of the cat, ferret, and rat: a light and electron microscopical study. Brain Research 676, 80-92 (1995).
43. Wolff, S D & Balaban. R S. Magnetization transfer contrast (MTC) and tissue water proton relaxation in vivo. Magn. Reson. Med. 10, 135-144. 1989
44. Wolff S D & Balaban, R S. Magnetization transfer imaging: practical aspects and clinical applications. Radiology, 192, 593-599, 1994.
45. Kurki T, Lundbom N, Kalimo H and Valtonen S. MR classification of brain gliomas: value of magnetization transfer and conventional imaging, Miagn, Reson, Imaging, 13, 501-511, 1995.
46. Lee K H & Contache D A (1995) Detection of β-actin mRNA by RT-PCR in normal and regenerating chicken cochleae. Hearing Research. 87, 9-15.
47. McNeight, S L (1980) Nucleic Acids Research S, 5949-5964.
48. Gerdes, C A, Castro, M G. Lowenstein, P R (2000) Molecular Therapy (in press).

The invention claimed is:

1. A method for the treatment of a tumor in an individual by suicide gene therapy, the method comprising:
co-administering an adenovirus expressing the suicide gene, encoding a cytotoxic pro-drug converting enzyme under the control of an expression control sequence, directly into the tumor of the individual, and a cytotoxic pro-drug that effectively treats the tumor in the individual; and
repeating the administration of said cytotoxic pro-drug to the individual, wherein said repeating is at three months or more after the co-administration, and
wherein the cytotoxic pro-drug comprises ganciclovir.

2. The method according to claim 1, wherein said repeating the administration of said cytotoxic pro-drug is at, three months, four months, six months, eight months, ten months or twelve months or fractions thereof.

3. The method of claim 1, wherein the suicide gene comprises HSV1-TK coding sequences.

4. The method of claim 1, wherein the tumor is a brain glioma.

5. A method of increasing the effectiveness of a cytotoxic pro-drug in an individual in need thereof, the method comprising:
providing an adenovirus vector, encoding HSV1-TK under the control of an expression control sequence; and
co-administering, to the individual, the adenovirus vector with a first cycle of said cytotoxic pro-drug, said cytotoxic pro-drug being administered to the individual at additional cycles, wherein at least one cycle is at three months or more after the co-administration, wherein the cytotoxic pro-drug comprises ganciclovir.

6. A method of causing regression of tumor size in an individual in need thereof, the method comprising:
co-administering an adenovirus vector, encoding HSV1-TK under the control of an expression control sequence directly into said tumor of the individual, and ganciclovir, wherein said ganciclovir is administered to the individual at additional cycles, and at least one cycle is at three months or more after the co-administration.

7. A method for the treatment of a tumor in an individual by suicide gene therapy, the method comprising:
co-administrating an adenovirus vector, encoding HSV1-TK under the control of an expression control sequence directly into the tumor of the individual, and
ganciclovir to the individual; and
repeating the administration of said ganciclovir to the individual, wherein said repeating is at three months or more after the co-administration.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer A

<400> SEQUENCE: 1
aagcaagtgt cttgctgtct                                           20

<210> SEQ ID NO 2
<211> LENGTH: 20
<212> TYPE: DNA
<213> ORGANISM: Artificial Sequence
<220> FEATURE:
<223> OTHER INFORMATION: Primer B

<400> SEQUENCE: 2

```
ggatggaacc attataccgc                                              20

<210> SEQ ID NO 3
<211> LENGTH: 24
<212> TYPE: DNA
<213> ORGANISM: Artificial Sequence
<220> FEATURE:
<223> OTHER INFORMATION: Primer C

<400> SEQUENCE: 3
caagaatcgc ctgctactgt tgtc                                         24

<210> SEQ ID NO 4
<211> LENGTH: 25
<212> TYPE: DNA
<213> ORGANISM: Artificial Sequence
<220> FEATURE:
<223> OTHER INFORMATION: Primer D

<400> SEQUENCE: 4
cctatcctcc gtatctatct ccacc                                        25

<210> SEQ ID NO 5
<211> LENGTH: 20
<212> TYPE: DNA
<213> ORGANISM: Artificial Sequence
<220> FEATURE:
<223> OTHER INFORMATION: Primer E

<400> SEQUENCE: 5
aaaaccacca ccacgcaact                                              20

<210> SEQ ID NO 6
<211> LENGTH: 20
<212> TYPE: DNA
<213> ORGANISM: Artificial Sequence
<220> FEATURE:
<223> OTHER INFORMATION: Primer F

<400> SEQUENCE: 6
gtcatgctgc ccataaggta                                              20

<210> SEQ ID NO 7
<211> LENGTH: 22
<212> TYPE: DNA
<213> ORGANISM: Artificial Sequence
<220> FEATURE:
<223> OTHER INFORMATION: Primer G

<400> SEQUENCE: 7
ccagccatgt acgtagccat cc                                           22

<210> SEQ ID NO 8
<211> LENGTH: 23
<212> TYPE: DNA
<213> ORGANISM: Artificial Sequence
<220> FEATURE:
<223> OTHER INFORMATION: Primer H

<400> SEQUENCE: 8
gcagctcata gctcttctcc agg                                          23
```